United States Patent
Coleman et al.

(10) Patent No.: US 7,091,020 B1
(45) Date of Patent: *Aug. 15, 2006

(54) HUMAN JAK2 KINASE

(75) Inventors: Roger Coleman, Mountain View, CA (US); Susan G. Stuart, Montara, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/467,100

(22) Filed: Dec. 10, 1999

Related U.S. Application Data

(62) Division of application No. 09/196,480, filed on Nov. 19, 1998, now Pat. No. 6,019,966, which is a division of application No. 08/567,508, filed on Dec. 5, 1995, now Pat. No. 5,914,393.

(51) Int. Cl.
*C12N 9/12* (2006.01)
*C07H 21/04* (2006.01)

(52) U.S. Cl. .......................... 435/194; 435/183; 435/6; 530/350; 536/23.1; 536/23.2; 424/94.5

(58) Field of Classification Search ................ 435/183, 435/6, 194; 530/350; 424/94.5
See application file for complete search history.

(56) References Cited

U.S. PATENT DOCUMENTS 5,716,818 A  2/1998  Wilks et al. ................ 435/194

OTHER PUBLICATIONS

Wilks et al. Two novel Protein-Tyrosine Kinases, Each with a Second Phosphotransferase-related Catalytic Domain, Define a New Class of Protein Kinase, Mol. Cell. Biol. 11 (4): 2057-2065, Apr. 1991.*
Taniguchi, T., "Cytokine Signaling Through Nonreceptor Protein Tyrosine Kinases," *Science*, 268:251-255 (1995).
David, M. et al., "Requirement for MAP Kinase (ERK2) Activity in Interferon α- and Interferon β-Stimulated Gene Expression Through STAT Proteins," *Science*, 269:1721-1723 (1995).
Herrera-Gonzalez and Dresser, "Fetal-Maternal Immune Interaction: Blocking Antibody and Survival of Fetus," *Dev. Comp. Immunol.*, 17(1):1-18 (1993).
Mitchell et al., "Cytokine Networking in the Placenta," *Placenta*, 14:249-275 (1993).
Rutanen, "Cytokines in Reproduction," *Ann. Med.* 25:343-347 (1993).
Strosberg, A.D. et al., "Functional Expression of Receptors in Microorganisms", *Trends in Pharmacological Sciences*, 13(3):95-98, 1992.
Grynkiewicz, G. et al., "A New Generation of $Ca^{2+}$ Indicators with Greatly Improved Fluorescence Properties," *The Journal of Biological Chemistry*, 260(3):3440-3450, 1985.
McColl, S. et al., "Uncoupling of Early Signal Transduction Events from Effector Function in Human Peripheral Blood Neutrophils in Response to Recombinant Macrophage Inflammatory Proteins-1α and -1β," *The Journal of Immunology*, 150:4550-4560 (1993).
Wilks, A .F., "Two putative protein-tyrosine kinases identified by application of the polymerase chain reaction," *Proc. Nalt. Acad. Sci. USA*, PNAS 86:1603-7 (1989).
Silvennoinen, B.A. et al., "Structure of the murine Jak2 protein-tyrosine kinase and its role in interleuikin 3 signal transduction," *Proc. Natl. Acad. Sci. USA* , PNAS 90:8429-8433 (1993).
Kawamura, M. et al., "Molecular cloning of L-JAK, a Janus family protein-tyrosine kinase expressed in natural killer cells and activated leukocytes", *Proc. Natl. Acad. Sci. USA*, 91:6374-6378 (1994).
Saltzman, A. et al., "Cloning and Characterization of Human Jak-2 Kinase: High mRNA Expression in Immune Cells and Muscle Tissue", *Biochem. Boiphys. Res. Comm.*, 246:627-633 (1998).
Dalal, I. et al., "Cloning and Characterization of the Human Homolog of Mouse JAK2", *Blood*, 91(3):844-851 (1998).
Nierman et al., eds., ATCC/NIH Repository Catalog of Human and Mouse DNA Probes and Libraries, Eighth Edition, pp. 1-70 (1994).

* cited by examiner

*Primary Examiner*—Richard Hutson
(74) *Attorney, Agent, or Firm*—Foley & Lardner LLP

(57) ABSTRACT

The present invention provides a polynucleotide (hjak2) which identifies and encodes a novel human Jak2 kinase (HJAK2) which was expressed in the placenta. The present invention also provides for antisense molecules and oligomers designed from the nucleotide sequence or its antisense. The invention further provides genetically engineered expression vectors and host cells for the production of purified HJAK2 peptide, antibodies capable of binding to HJAK2, inhibitors which bind to HJAK2 and pharmaceutical compositions based on HJAK2 specific antibodies or inhibitors. The invention specifically provides for diagnostic assays based on altered hjak2 expression and which allow identification of such a condition. These assays utilize probes which comprise oligomers, fragments, or portions of hjak2 or its regulatory elements or antibodies specifically binding HJAK2.

6 Claims, 12 Drawing Sheets

```
                348          357          366          375          384          393
5' ATG GGA ATG GCC TGC CTT ACG ATG ACA GAA ATG GAG GGA ACA TCC ACC TCT TCT
   Met Gly Met Ala Cys Leu Thr Met Thr Glu Met Glu Gly Thr Ser Thr Ser Ser 402          411          420          429          438          447
   ATA TAT CAG AAT GGT GAT ATT TCT GGA AAT GCC AAT TCT ATG AAG CAA ATA GAT
   Ile Tyr Gln Asn Gly Asp Ile Ser Gly Asn Ala Asn Ser Met Lys Gln Ile Asp 456          465          474          483          492          501
   CCA GTT CTT CAG GTG TAT CTT TAC CAT TCC CTT GGG AAA TCT GAG GCA GAT TAT
   Pro Val Leu Gln Val Tyr Leu Tyr His Ser Leu Gly Lys Ser Glu Ala Asp Tyr 510          519          528          537          546          555
   CTG ACC TTT CCA TCT GGG GAG TAT GTT GGA GAA GAA ATC TGT ATT GCT GCT TCT
   Leu Thr Phe Pro Ser Gly Glu Tyr Val Gly Glu Glu Ile Cys Ile Ala Ala Ser 564          573          582          591          600          609
   AAA GCT TGT GGT ATC ACA CCT GTG TAT CAT AAT ATG TTT GCT TTA ATG AGT GAA
   Lys Ala Cys Gly Ile Thr Pro Val Tyr His Asn Met Phe Ala Leu Met Ser Glu 618          627          636          645          654          663
   ACA GAA AGG ATC TGG TAT CCA CCC AAC CAT GTC TTC CAT ATA GAT GAG TCA ACC
   Thr Glu Arg Ile Trp Tyr Pro Pro Asn His Val Phe His Ile Asp Glu Ser Thr 672          681          690          699          708          717
   AGG CAT AAT GTA CTC TAC AGA ATA AGA TTT TAC TTT CCT CGT TGG TAT TGC AGT
   Arg His Asn Val Leu Tyr Arg Ile Arg Phe Tyr Phe Pro Arg Trp Tyr Cys Ser 726          735          744          753          762          771
   GGC AGC AAC AGA GCC TAT CGG CAT GGA ATA TCT CGA GGT GCT GAA GCT CCT CTT
   Gly Ser Asn Arg Ala Tyr Arg His Gly Ile Ser Arg Gly Ala Glu Ala Pro Leu 780          789          798          807          816          825
   CTT GAT GAC TTT GTC ATG TCT TAC CTC TTT GCT CAG TGG CGG CAT GAT TTT GTG
   Leu Asp Asp Phe Val Met Ser Tyr Leu Phe Ala Gln Trp Arg His Asp Phe Val 834          843          852          861          870          879
   CAT GGA TGG ATA AAA GTA CCT GTG ACT CAT GAA ACA CAG GAA GAA TGT CTT GGG
   His Gly Trp Ile Lys Val Pro Val Thr His Glu Thr Gln Glu Glu Cys Leu Gly 888          897          906          915          924          933
   ATG ACA GTG TTA GAT ATG ATG AGA ATA GCC AAA GAA AAC GAT CAA ACC CCA CTG
   Met Thr Val Leu Asp Met Met Arg Ile Ala Lys Glu Asn Asp Gln Thr Pro Leu 942          951          960          969          978          987
   GCC ATC TAT AAC TCT ATC AGC TAC AAG ACA TTC TTA CCA CAA TGT ATT CGA GCA
   Ala Ile Tyr Asn Ser Ile Ser Tyr Lys Thr Phe Leu Pro Gln Cys Ile Arg Ala
```

FIGURE 1A

```
      996            1005           1014           1023           1032           1041
AAG ATC CAA GAC TAT CAT ATT TTG ACA AGG AAG CGA ATA AGG TAC AGA TTT CGC
Lys Ile Gln Asp Tyr His Ile Leu Thr Arg Lys Arg Ile Arg Tyr Arg Phe Arg 1050           1059           1068           1077           1086           1095
AGA TTT ATT CAG CAA TTC AGC CAA TGC AAA GCC ACT GCC AGA AAC TTG AAA CTT
Arg Phe Ile Gln Gln Phe Ser Gln Cys Lys Ala Thr Ala Arg Asn Leu Lys Leu 1104           1113           1122           1131           1140           1149
AAG TAT CTT ATA AAT CTG GAA ACT CTG CAG TCT GCC TTC TAC ACA GAG AAA TTT
Lys Tyr Leu Ile Asn Leu Glu Thr Leu Gln Ser Ala Phe Tyr Thr Glu Lys Phe 1158           1167           1176           1185           1194           1203
GAA GTA AAA GAA CCT GGA AGT GGT CCT TCA GGT GAG GAG ATT TTT GCA ACC ATT
Glu Val Lys Glu Pro Gly Ser Gly Pro Ser Gly Glu Glu Ile Phe Ala Thr Ile 1212           1221           1230           1239           1248           1257
ATA ATA ACT GGA AAC GGT GGA ATT CAG TGG TCA AGA GGG AAA CAT AAA GAA AGT
Ile Ile Thr Gly Asn Gly Gly Ile Gln Trp Ser Arg Gly Lys His Lys Glu Ser 1266           1275           1284           1293           1302           1311
GAG ACA CTG ACA GAA CAG GAT TTA CAG TTA TAT TGC GAT TTT CCT AAT ATT ATT
Glu Thr Leu Thr Glu Gln Asp Leu Gln Leu Tyr Cys Asp Phe Pro Asn Ile Ile 1320           1329           1338           1347           1356           1365
GAT GTC AGT ATT AAG CAA GCA AAC CAA GAG GGT TCA AAT GAA AGC CGA GTT GTA
Asp Val Ser Ile Lys Gln Ala Asn Gln Glu Gly Ser Asn Glu Ser Arg Val Val 1374           1383           1392           1401           1410           1419
ACT ATC CAT AAG CAA GAT GGT AAA AAT CTG GAA ATT GAA CTT AGC TCA TTA AGG
Thr Ile His Lys Gln Asp Gly Lys Asn Leu Glu Ile Glu Leu Ser Ser Leu Arg 1428           1437           1446           1455           1464           1473
GAA GCT TTG TCT TTC GTG TCA TTA ATT GAT GGA TAT TAT AGA TTA ACT GCA GAT
Glu Ala Leu Ser Phe Val Ser Leu Ile Asp Gly Tyr Tyr Arg Leu Thr Ala Asp 1482           1491           1500           1509           1518           1527
GCA CAT CAT TAC CTC TGT AAA GAA GTA GCA CCT CCA GCC GTG CTT GAA AAT ATA
Ala His His Tyr Leu Cys Lys Glu Val Ala Pro Pro Ala Val Leu Glu Asn Ile 1536           1545           1554           1563           1572           1581
CAA AGC AAC TGT CAT GGC CCA ATT TCG ATG GAT TTT GCC ATT AGT AAA CTG AAG
Gln Ser Asn Cys His Gly Pro Ile Ser Met Asp Phe Ala Ile Ser Lys Leu Lys 1590           1599           1608           1617           1626           1635
AAA GCA GGT AAT CAG ACT GGA CTG TAT GTA CTT CGA TGC AGT CCT AAG GAC TTT
Lys Ala Gly Asn Gln Thr Gly Leu Tyr Val Leu Arg Cys Ser Pro Lys Asp Phe
```

FIGURE 1B

```
        1644            1653            1662            1671            1680            1689
AAT AAA TAT TTT TTG ACT TTT GCT GTC GAG CGA GAA AAT GTC ATT GAA TAT AAA
Asn Lys Tyr Phe Leu Thr Phe Ala Val Glu Arg Glu Asn Val Ile Glu Tyr Lys 1698            1707            1716            1725            1734            1743
CAC TGT TTG ATT ACA AAA AAT GAG AAT GAA GAG TAC AAC CTC AGT GGG ACA AAG
His Cys Leu Ile Thr Lys Asn Glu Asn Glu Glu Tyr Asn Leu Ser Gly Thr Lys 1752            1761            1770            1779            1788            1797
AAG AAC TTC AGC AGT CTT AAA GAT CTT TTG AAT TGT TAC CAG ATG GAA ACT GTT
Lys Asn Phe Ser Ser Leu Lys Asp Leu Leu Asn Cys Tyr Gln Met Glu Thr Val 1806            1815            1824            1833            1842            1851
CGC TCA GAC AAT ATA ATT TTC CAG TTT ACT AAA TGC TGT CCC CCA AAG CCA AAA
Arg Ser Asp Asn Ile Ile Phe Gln Phe Thr Lys Cys Cys Pro Pro Lys Pro Lys 1860            1869            1878            1887            1896            1905
GAT AAA TCA AAC CTT CTA GTC TTC AGA ACG AAT GGT GTT TCT GAT GTA CCA ACC
Asp Lys Ser Asn Leu Leu Val Phe Arg Thr Asn Gly Val Ser Asp Val Pro Thr 1914            1923            1932            1941            1950            1959
TCA CCA ACA TTA CAG AGG CCT ACT CAT ATG AAC CAA ATG GTG TTT CAC AAA ATC
Ser Pro Thr Leu Gln Arg Pro Thr His Met Asn Gln Met Val Phe His Lys Ile 1968            1977            1986            1995            2004            2013
AGA AAT GAA GAT TTG ATA TTT AAT GAA AGC CTT GGC CAA GGC ACT TTT ACA AAG
Arg Asn Glu Asp Leu Ile Phe Asn Glu Ser Leu Gly Gln Gly Thr Phe Thr Lys 2022            2031            2040            2049            2058            2067
ATT TTT AAA GGC GTA CGA AGA GAA GTA GGA GAC TAC GGT CAA CTG CAT GAA ACA

Ile Phe Lys Gly Val Arg Arg Glu Val Gly Asp Tyr Gly Gln Leu His Glu Thr 2076            2085            2094            2103            2112            2121
GAA GTT CTT TTA AAA GTT CTG GAT AAA GCA CAC AGG AAC TAT TCA GAG TCT TTC
Glu Val Leu Leu Lys Val Leu Asp Lys Ala His Arg Asn Tyr Ser Glu Ser Phe 2130            2139            2148            2157            2166            2175
TTT GAA GCA GCA AGT ATG ATG AGC AAG CTT TCT CAC AAG CAT TTG GTT TTA AAT
Phe Glu Ala Ala Ser Met Met Ser Lys Leu Ser His Lys His Leu Val Leu Asn 2184            2193            2202            2211            2220            2229
TAT GGA GTA TGT GTC TGT GGA GAC GAG AAT ATT CTG GTT CAG GAG TTT GTA AAA
Tyr Gly Val Cys Val Cys Gly Asp Glu Asn Ile Leu Val Gln Glu Phe Val Lys 2238            2247            2256            2265            2274            2283
TTT GGA TCA CTA GAT ACA TAT CTG AAA AAG AAT AAA AAT TGT ATA AAT ATA TTA
Phe Gly Ser Leu Asp Thr Tyr Leu Lys Lys Asn Lys Asn Cys Ile Asn Ile Leu
```

FIGURE 1C

```
        2292            2301            2310            2319            2328            2337
TGG AAA CTT GAA GTT GCT AAA CAG TTG GCA TGG GCC ATG CAT TTT CTA GAA GAA
Trp Lys Leu Glu Val Ala Lys Gln Leu Ala Trp Ala Met His Phe Leu Glu Glu 2346            2355            2364            2373            2382            2391
AAC ACC CTT ATT CAT GGG AAT GTA TGT GCC AAA AAT ATT CTG CTT ATC AGA GAA
Asn Thr Leu Ile His Gly Asn Val Cys Ala Lys Asn Ile Leu Leu Ile Arg Glu 2400            2409            2418            2427            2436            2445
GAA GAC AGG AAG ACA GGA AAT CCT CCT TTC ATC AAA CTT AGT GAT CCT GGC ATT
Glu Asp Arg Lys Thr Gly Asn Pro Pro Phe Ile Lys Leu Ser Asp Pro Gly Ile 2454            2463            2472            2481            2490            2499
AGT ATT ACA GTT TTG CCA AAG GAC ATT CTT CAG GAG AGA ATA CCA TGG GTA CCA
Ser Ile Thr Val Leu Pro Lys Asp Ile Leu Gln Glu Arg Ile Pro Trp Val Pro 2508            2517            2526            2535            2544            2553
CCT GAA TGC ATT GAA AAT CCT AAA AAT TTA AAT TTG GCA ACA GAC AAA TGG AGT
Pro Glu Cys Ile Glu Asn Pro Lys Asn Leu Asn Leu Ala Thr Asp Lys Trp Ser 2562            2571            2580            2589            2598            2607
TTT GGT ACC ACT TTG TGG GAA ATC TGC AGT GGA GGA GAT AAA CCT CTA AGT GCT
Phe Gly Thr Thr Leu Trp Glu Ile Cys Ser Gly Gly Asp Lys Pro Leu Ser Ala 2616            2625            2634            2643            2652            2661
CTG GAT TCT CAA AGA AAG CTA CAA TTT TAT GAA GAT AGG CAT CAG CTT CCT GCA
Leu Asp Ser Gln Arg Lys Leu Gln Phe Tyr Glu Asp Arg His Gln Leu Pro Ala 2670            2679            2688            2697            2706            2715
CCA AAG TGG GCA GAA TTA GCA AAC CTT ATA AAT AAT TGT ATG GAT TAT GAA CCA
Pro Lys Trp Ala Glu Leu Ala Asn Leu Ile Asn Asn Cys Met Asp Tyr Glu Pro 2724            2733            2742            2751            2760            2769
GAT TTC AGG CCT TCT TTC AGA GCC ATC ATA CGA GAT CTT AAC AGT TTG TTT ACT
Asp Phe Arg Pro Ser Phe Arg Ala Ile Ile Arg Asp Leu Asn Ser Leu Phe Thr 2778            2787            2796            2805            2814            2823
CCA GAT TAT GAA CTA TTA ACA GAA AAT GAC ATG TTA CCA AAT ATG AGG ATA GGT
Pro Asp Tyr Glu Leu Leu Thr Glu Asn Asp Met Leu Pro Asn Met Arg Ile Gly 2832            2841            2850            2859            2868            2877
GCC TTG GGG TTT TCT GGT GCC TTT GAA GAC CGG GAT CCT ACA CAG TTT GAA GAG
Ala Leu Gly Phe Ser Gly Ala Phe Glu Asp Arg Asp Pro Thr Gln Phe Glu Glu 2886            2895            2904            2913            2922            2931
```

FIGURE 1D

```
AGA CAT TTG AAA TTT CTA CAG CAA CTT GGC AAG GGT AAT TTT GGG AGT GTG GAG
Arg His Leu Lys Phe Leu Gln Gln Leu Gly Lys Gly Asn Phe Gly Ser Val Glu 2940        2949        2958        2967        2976        2985
ATG TGC CGG TAT GAC CCT CTA CAG GAC AAC ACT GGG GAG GTG GTC GCT GTA AAA
Met Cys Arg Tyr Asp Pro Leu Gln Asp Asn Thr Gly Glu Val Val Ala Val Lys 2994        3003        3012        3021        3030        3039
AAG CTT CAG CAT AGT ACT GAA GAG CAC CTA AGA GAC TTT GAA AGG GAA ATT GAA
Lys Leu Gln His Ser Thr Glu Glu His Leu Arg Asp Phe Glu Arg Glu Ile Glu 3048        3057        3066        3075        3084        3093
ATC CTG AAA TCC CTA CAG CAT GAC AAC ATT GTA AAG TAC AAG GGA GTG TGC TAC
Ile Leu Lys Ser Leu Gln His Asp Asn Ile Val Lys Tyr Lys Gly Val Cys Tyr 3102        3111        3120        3129        3138        3147
AGT GCT GGT CGG CGT AAT CTA AAA TTA ATT ATG GAA TAT TTA CCA TAT GGA AGT
Ser Ala Gly Arg Arg Asn Leu Lys Leu Ile Met Glu Tyr Leu Pro Tyr Gly Ser 3156        3165        3174        3183        3192        3201
TTA CGA GAC TAT CTT CAA AAA CAT AAA GAA CGG ATA GAT CAC ATA AAA CTT CTG
Leu Arg Asp Tyr Leu Gln Lys His Lys Glu Arg Ile Asp His Ile Lys Leu Leu 3210        3219        3228        3237        3246        3255
CAG TAC ACA TCT CAG ATA TGC AAG GGT ATG GAG TAT CTT GGT ACA AAA AGG TAT
Gln Tyr Thr Ser Gln Ile Cys Lys Gly Met Glu Tyr Leu Gly Thr Lys Arg Tyr 3264        3273        3282        3291        3300        3309
ATC CAC AGG GAT CTG GCA ACG AGA AAT ATA TTG GTG GAG AAC GAG AAC AGA GTT
Ile His Arg Asp Leu Ala Thr Arg Asn Ile Leu Val Glu Asn Glu Asn Arg Val 3318        3327        3336        3345        3354        3363
AAA ATT GGA GAT TTT GGG TTA ACC AAA GTC TTG CCA CAA GAC AAA GAA TAC TAT
Lys Ile Gly Asp Phe Gly Leu Thr Lys Val Leu Pro Gln Asp Lys Glu Tyr Tyr 3372        3381        3390        3399        3408        3417
AAA GTA AAA GAA CCT GGT GAA AGT CCC ATA TTC TGG TAT GCT CCA GAA TCA CTG
Lys Val Lys Glu Pro Gly Glu Ser Pro Ile Phe Trp Tyr Ala Pro Glu Ser Leu 3426        3435        3444        3453        3462        3471
ACA GAG AGC AAG TTT TCT GTG GCC TCA GAT GTT TGG AGC TTT GGA GTG GTT CTG
Thr Glu Ser Lys Phe Ser Val Ala Ser Asp Val Trp Ser Phe Gly Val Val Leu 3480        3489        3498        3507        3516        3525
TAT GAA CTT TTC ACA TAC ATT GAG AAG AGT AAA AGT CCA CCA GCG GAA TTT ATG
Tyr Glu Leu Phe Thr Tyr Ile Glu Lys Ser Lys Ser Pro Pro Ala Glu Phe Met 3534        3543        3552        3561        3570        3579
CGT ATG ATT GGC AAT GAC AAA CAA GGA CAG ATG ATC GTG TTC CAT TTG ATA GAA
Arg Met Ile Gly Asn Asp Lys Gln Gly Gln Met Ile Val Phe His Leu Ile Glu
```

FIGURE 1E

```
        3588            3597            3606            3615            3624            3633
CTT TTG AAG AAT AAT GGA AGA TTA CCA AGA CCA GAT GGA TGC CCA GAT GAG ATC
Leu Leu Lys Asn Asn Gly Arg Leu Pro Arg Pro Asp Gly Cys Pro Asp Glu Ile 3642            3651            3660            3669            3678            3687
TAT ATG ATC ATG ACA GAA TGC TGG AAC AAT AAT GTA AAT CAA CGC CCC TCC TTT
Tyr Met Ile Met Thr Glu Cys Trp Asn Asn Asn Val Asn Gln Arg Pro Ser Phe 3696            3705            3714            3723            3732
AGG GAT CTA GCT CTT CGA GTG GAT CAA ATA AGG GAT AAC ATG GCT GGA TGA   3'
Arg Asp Leu Ala Leu Arg Val Asp Gln Ile Arg Asp Asn Met Ala Gly ***
```

HUMAN JAK2 KINASE

This application is a divisional application of U.S. application Ser. No. 09/196,480, filed Nov. 19, 1998, now U.S. Pat. No. 6,019,966 which is a divisional of U.S. application Ser. No. 08/567,508, filed Dec. 5, 1995, issued Jun. 22, 1999, as U.S. Pat. No. 5,914,393.

FIELD OF THE INVENTION

The present invention relates to a novel, human Jak2 kinase isolated from human placenta and to the use of this novel protein and its nucleic acid sequence in the diagnosis, study, prevention, and treatment of disease.

BACKGROUND OF THE INVENTION

JAK kinases are Janus family nonreceptor protein-tyrosine kinases (NR-PTK) that lack transmembrane regions and form functional complexes with the intercellular regions of other cell surface receptors. They were first identified as the products of mutant oncogenes in cancer cells where their activation was no longer subject to normal cellular controls. Described JAK kinases include Jak1, Jak2, and Jak3, which all share the conserved kinase domain. In addition, these proteins have 5 to 100 amino acid residues located on either side of, or inserted into loops of, the carboxyterminal kinase domain which allow the regulation of each kinase as it recognizes and interacts with its target protein. Known target proteins include growth hormone receptor, prolactin receptor, erythropoietin receptor, cytokine receptors and others which utilize the common chain known as gp130. These receptors are unique both in their ability to recruit multiple PTKs and in the diversity of their responses within different cell types (Taniguchi T (1995) Science 268:251–55). Genetic evidence places these kinases in the interferon α and γ signal transduction pathways which are widely expressed in mammalian cells.

Kinases regulate many different cell proliferation, differentiation, and signaling processes by adding phosphate groups to proteins. The high energy phosphate which drives activation is generally transferred from adenosine triphosphate molecules (ATP) to a particular protein by the PTKs, and the transfer process is roughly analogous to turning on a molecular switch. When the switch goes on, the kinase activates a metabolic enzyme, regulatory protein, receptor, cytoskeletal protein, ion channel or pump, transcription factor, or another kinase. For example, in their normal role, the JAK NR-PTKs are capable of regulating tyrosine phosphorylation of STAT proteins, signal transducers and activators of transcription, such that they translocate to the nucleus and bind DNA (David M et al. (1995) Science 269:1721–1723). In contrast, uncontrolled kinase signaling has been implicated in inflammation, oncogenesis, arteriosclerosis, and psoriasis.

Almost all kinases contain a similar 250–300 amino acid catalytic domain. The N-terminal domain generally folds into a two-lobed structure to bind and orient ATP (or GTP) donor molecules. The larger C terminal lobe binds the protein substrate and carries out the transfer of phosphate from ATP to the hydroxyl group of a tyrosine residue. The primary structure of the kinase domain is conserved in the residues: $G_{50}$ and $G_{52}$ in subdomain I, $K_{72}$ in subdomain II, $G_{91}$ in subdomain III, $E_{208}$ in subdomain VIII, $D_{220}$ and $G_{225}$, in subdomain IX, and the amino acid motifs of subdomain VIB, VIII and IX (Hardie G and Hanks S (1995) Academic Press, San Diego Calif.).

The novel human Jak2 kinase, hjak2, of the present application shows significant conservation of the diagnostic kinase residues which allowed its identification from among the isolated cDNAs of a placenta library, the anatomy and physiology of which is briefly described below.

The placenta is a thickened disk-shaped temporary organ that interchanges gases, nutrients, hormones, excretory products, humoral antibodies (IgG), and any other circulating substances between the maternal and fetal bloodstreams. Receptors facilitate the transport of glucose, amino acids, and IgG directly from maternal blood to fetal blood. The placenta is the only organ composed of cells derived from two individuals, the fetal extraembryonic chorion and the maternal endometrium. The boundary between these two tissues is marked by extracellular products of necrosis referred to as fibrinoid. This boundary results from the various tissue interactions, immunological responses, etc. which occur in the placenta.

The major tissue interaction involves the expression of paternal antigens by the chorionic villi which is directly adjacent to maternal blood. Although the mother initiates an immunological response, fetal tissue is not typically rejected. This is attributed to the fact that the fetus only expresses major histocompatibility complex (MHC) I, and not MHC II which is the major cause of organ allograft rejection. In addition, uterine secretions during early gestation contain significant amounts of glucose and glycoproteins which may participate in local immunosuppression. Although infections by bacteria, viruses, mycoplasmas, or parasites may ascend from the endocervical canal or reach the placenta through maternal blood, they rarely cause gross pathological changes because of maternal immune defense.

Soon after implantation, fetal villi begin to control maternal physiology to create an optimal environment for development. This involves the production of chorionic gonadotropin, estrogen and progesterone, chorionic somatomammotropin, insulin-like growth factors, platelet derived growth factor, prolactin, and various cytokines. These and other factors such as hjak2 certainly regulate the numerous activities (respiratory, immunological, gastrointestinal, and urinary) which occur within the placenta and between maternal and fetal tissues.

The anatomy and physiology of human placenta is reviewed, inter alia, in Benirschke and Kaufmann, (1992) *Pathology of the Human Placenta*, Springer-Verlag, New York N.Y., pp. 542–635; Herrera Gonzalez and Dresser (1993) Dev Comp Immunol 17(1):1–18; Mitchell et al. (1993) Placenta 14:249–275; Naeye (1992) *Disorders of the Placenta, Fetus, and Neonate; Diagnosis and Clinical Significance*, Moseby Year Book, St. Louis Mo.; and Rutanen (1993) Ann Med 25:343–347.

SUMMARY

The present invention relates to a novel human Jak2 kinase and to the use of the protein and its nucleic acid sequence in the study, diagnosis, prevention, and treatment of diseases. Human Jak2 kinase (hjak2) was first identified as a partial nucleotide sequence in Incyte Clone 179527 during a computer search for nucleotide sequence alignments among the cDNAs of a placenta library. A modified XL-PCR procedure, specially designed oligonucleotides, and cDNAs of the placenta library were used to extend Incyte Clone 179527 to full length. The assembled nucleotide sequence (SEQ ID NO: 1) hjak2 encodes the polypeptide (SEQ ID NO: 2) HJAK2 (SEQ ID NO: 2). Computer search and alignment of the full length amino acid sequence showed that HJAK2 has 92% similarity to murine Jak2 kinase (MUSPTK1; GenBank GI 409584; Wilks A F (1989) Proc Nat Acad Sci 86:1603–7), which in turn has 96% sequence similarity with human Jak1 kinase. These homologies and the conserved residues, $G_{48}$, $K_{73}$, $E_{192}$, and $D_{220}$ which all lie within the catalytic domain contributed to the naming and uses of hjak2.

The complete nucleic acid sequence encoding hjak2 (SEQ ID NO: 1) disclosed herein, provides the basis for the design of antisense molecules useful in diminishing or eliminating expression of the genomic nucleotide sequence. For example, hjak2, or its oligonucleotides, fragments, portions, or complement, may be used in diagnostic hybridization or amplification assays of biopsied tissue to detect and/or quantify abnormalities in gene expression associated with an immunological disorder. The present invention also relates, in part, to the inclusion of the nucleic acid sequence in an expression vector which can be used to transform host cells or organisms. Such transgenic hosts are useful for production and recovery of the encoded HJAK2.

The invention further comprises using purified HJAK2 polypeptide to produce antibodies or to identify antagonists or inhibitors which bind HJAK2. Anti-HJAK antibodies may be used in membrane, tissue-based or ELISA technologies to detect any disease state or condition related to the aberrant expression of HJAK2. Antibodies, antagonists or inhibitors can be used to bind HJAK2 preventing the transfer of high energy phosphate molecules and therefore signal transduction. The invention also comprises pharmaceutical compositions containing the peptide, antibodies, antagonists or inhibitors for the diagnosis, prevention or treatment of conditions associated with altered or uncontrolled hjak2 expression. These conditions may include, but are not limited to: arteriosclerosis, asthma, bronchitis, emphysema, inflammatory bowel disease, leukemia, oncogenesis, osteoarthritis, psoriasis, rheumatoid arthritis, septic shock, and systemic lupus erythematosus. Steps for testing a biological sample with probes, oligomers, fragments or portions of the hjak2 nucleotide sequence or antibodies produced against the purified HJAK2 protein are provided.

Antisense molecules, antibodies, antagonists or inhibitors (including proteins, peptides, oligopeptides or organic molecules capable of compromising or modulating HJAK2 expression) may also be used for therapeutic purposes, for example, in neutralizing the aberrant activity of a HJAK2 associated with, for example, inflammation or oncogenesis. The present invention also provides for pharmaceutical compositions for the treatment of disease states associated with aberrant expression of hjak2 comprising the aforementioned antisense molecules, antibodies, antagonists or inhibitors.

DESCRIPTION OF THE FIGURES

FIGS. 1A, 1B, 1C, 1D, 1E, 1F, 1G, and 1H display displays an alignment of the nucleic acid (SEQ ID NO:1) and amino acid (SEQ ID NO:2) sequences of human jak2 kinase. Alignments shown in these and in the following figures were produced using the multisequence alignment program of DNASTAR software (DNASTAR Inc. Madison Wis.).

FIGS. 2A, 2B, 2C, 2D, 2E and 2F show the amino acid sequence similarity between HJAK2 (SEQ ID NO:2) and MUSPTK1 (GI 409584; SEQ ID NO:3).

DETAILED DESCRIPTION OF THE INVENTION

Definitions

As used herein, the abbreviation for the novel human Jak2 kinase in lower case (hjak2) refers to a gene, cDNA, RNA, or nucleic acid sequence, while the upper case version (HJAK2) refers to a protein, polypeptide, peptide, oligopeptide, or amino acid sequence.

An "oligonucleotide" or "oligomer" is a stretch of nucleotide residues which has a sufficient number of bases to be used in a polymerase chain reaction (PCR). These short sequences are based on (or designed from) genomic or cDNA sequences and are used to amplify, confirm, or reveal the presence of an identical, similar or complementary DNA or RNA in a particular cell or tissue. Oligonucleotides or oligomers comprise portions of a DNA sequence having at least about 10 nucleotides and as many as about nucleotides, preferably about 15 to 30 nucleotides. They are chemically synthesized and may be used as probes.

"Probes" are nucleic acid sequences of variable length, preferably between at least about 10 and as many as about 6,000 nucleotides. They are used in the detection of identical, similar, or complementary nucleic acid sequences. Longer length probes are usually obtained from a natural or recombinant source, are highly specific and much slower to hybridize than oligonucleotides. They may be single- or double-stranded and are carefully designed to have specificity in PCR, hybridization membrane-based, or ELISA-like technologies.

"Reporter" molecules are chemical moieties used for labelling a nucleic or amino acid sequence. They include, but are not limited to, radionuclides, enzymes, fluorescent, chemiluminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Recombinant nucleotide variants" are polynucleotides which encode a protein. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Linkers" are synthesized palindromic nucleotide sequences which create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, KpnI and Hind III or which provide a blunt end such as EcoRV, SnaBI and StuI.

"Control elements" or "regulatory sequences" are those nontranslated regions of the gene or DNA such as enhancers, promoters, introns and 3' untranslated regions which interact with cellular proteins to carry out replication, transcription, and translation. They may occur as boundary sequences or even split the gene. They function at the molecular level and along with regulatory genes are very important in development, growth, differentiation and aging processes.

"Chimeric" molecules are polynucleotides or polypeptides which are created by combining one or more of nucleotide sequences of this invention (or their parts) with additional nucleic acid sequence(s). Such combined sequences may be introduced into an appropriate vector and expressed to give rise to a chimeric polypeptide which may be expected to be different from the native molecule in one or more of the following characteristics: cellular location, distribution, ligand-binding affinities, interchain affinities, degradation/turnover rate, signalling, etc.

"Active" refers to those forms, fragments, or domains of an amino acid sequence which display the biologic and/or immunogenic activity characteristic of the naturally occurring peptide.

"Naturally occurring HJAK2" refers to a polypeptide produced by cells which have not been genetically engineered or which have been genetically engineered to produce the same sequence as that naturally produced. Specifically contemplated are various polypeptides which arise from post-translational modifications. Such modifications of the polypeptide include but are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring HJAK2 by amino acid-insertions, deletions and/or substitutions, created using recombinant DNA techniques. Guidance in determining which amino acid residues may be replaced, added or deleted without abolishing characteristics of interest may be found by comparing the sequence of HJAK2 with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the hjak2 sequence using recombinant DNA techniques.

A "signal or leader sequence" is a short amino acid sequence which or can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and either the same length as or considerably shorter than a "fragment", a "portion", or a "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, antagonists and their derivatives.

A "standard" is a quantitative or qualitative measurement use for comparison. Preferably, it is based on a statistically appropriate number of samples and is created to use as a basis of comparison when performing diagnostic assays, running clinical trials, or following patient treatment profiles. The samples of a particular standard may be normal or similarly abnormal.

"Animal" as used herein may be defined to include human, domestic (cats, dogs, etc.), agricultural (cows, horses, sheep, goats, chicken, fish, etc.), test species (frogs, mice, rats, rabbits, simians, etc.)

"Conditions" includes cancers, disorders or diseases in which hjak2 activity may be implicated. These specifically include, but are not limited to, anemia, arteriosclerosis, asthma, bronchitis, emphysema, gingivitis, inflammatory bowel disease, insulin-dependent diabetes mellitus leukemia, multiple endocrine neoplasias, osteoarthritis, osteoporosis, pulmonary fibrosis, rheumatoid arthritis, septic shock syndromes, and systemic lupus erythematosus.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

DESCRIPTION OF THE INVENTION

The present invention provides for a purified polynucleotide which encodes a novel human Jak2 kinase which is expressed in human cells or tissues. The human Jak2 kinase (hjak2; Incyte Clone 179527) was first identified among the cDNAs from a placenta cDNA library. The naming and proscribed uses of the present invention are based in part on the conserved residues found in HJAK2. These particularly include the residues $G_{48}$, $K_{73}$, $E_{192}$, and $D_{220}$, which are all found within the catalytic domain. Computer search and alignment of the full length amino acid sequences showed that HJAK2 has 92% similarity to murine Jak2 kinase (MUSPTK1; GenBank GI 409584; Wilks A F (1989) Proc Nat Acad Sci 86:1603–7), which in turn has 96% sequence similarity with human Jak1 kinase.

Purified nucleotide sequences, such as hjak2, have numerous applications in techniques known to those skilled in the art of molecular biology. These techniques include their use as PCR or hybridization probes, for chromosome and gene mapping, in the production of sense or antisense nucleic acids, in screening for new therapeutic molecules, etc. These examples are well known and are not intended to be limiting. Furthermore, the nucleotide sequences disclosed herein may be used in molecular biology techniques that have not yet been developed, provided the new techniques rely on properties of nucleotide sequences that are currently known, including, but not limited to, such properties as the triplet genetic code and specific base pair interactions.

As a result of the degeneracy of the genetic code, a multitude of HJAK2-encoding nucleotide sequences may be produced. Some of these will bear only minimal homology to the endogenous sequence of any known and naturally occurring Jak2 kinase sequence. This invention has specifically contemplated each and every possible variation of nucleotide sequence that could be made by selecting combinations based on possible codon choices. These combinations are made in accordance with the standard triplet genetic code as applied to the nucleotide sequence of naturally occurring HJAK2 and all such variations are to be considered as being specifically disclosed.

Although the hjak2 nucleotide sequence and its derivatives or variants are preferably capable of identifying the nucleotide sequence of the naturally occurring HJAK2 under optimized conditions, it may be advantageous to produce HJAK2-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding the HJAK2 without altering the encoded amino acid sequence include the production of RNA transcripts having more desirable properties, such as a longer half-life, than transcripts produced from the naturally occurring sequence.

Nucleotide sequences encoding HJAK2 may be joined to a variety of 26 other nucleotide sequences by means of well established recombinant DNA techniques (Sambrook J et al (1989) *Molecular Cloning: A Laboratory Manual*, Cold Spring Harbor Laboratory, Cold Spring Harbor N.Y., Chapters 4, 8, 16, and 17 or Ausubel FM et al (1989) *Current Protocols in Molecular Biology*, John Wiley & Sons, New York New York N.Y., Chapters 9, 13, and 16). Useful sequences for joining to hjak2 include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR as described in U.S. Pat. Nos. 4,683,195; 4,800,195; and 4,965,188 provides additional uses for oligonucleotides based upon the hjak2 nucleotide sequence. Such oligomers are generally chemically synthesized, but they may be of recombinant origin or a mixture of both. Oligomers generally comprise two nucleotide sequences, one with sense orientation (5'->3') and one with antisense orientation (3' to 5') employed under optimized conditions for identification of a specific gene or diagnostic use. The same two oligomers, nested sets of oligomers, or even a degenerate pool of oligomers may be employed under less stringent conditions for identification and/or quantitation of closely related DNA or RNA sequences.

Full length genes may be cloned utilizing partial nucleotide sequence and various methods known in the art. Sarkar (1993; PCR Methods Applic 2:318–22) disclose "restriction-site PCR" as a direct method which uses universal primers to retrieve unknown sequence adjacent to a known locus. First, genomic DNA is amplified in the presence of primer to linker and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase. Sarkar present data concerning Factor IX for which they identified a conserved stretch of 20 nucleotides in the 3' noncoding region of the gene.

Inverse PCR is the first method to report successful acquisition of unknown sequences starting with primers based on a known region (Triglia T 26 et al (1988) Nucleic Acids Res 16:8186). The method uses several restriction enzymes to generate a suitable fragment in the known region of a gene. The fragment is then circularized by intramolecular ligation and used as a PCR template. Divergent primers are designed from the known region. The multiple rounds of restriction enzyme digestions and ligations that are necessary prior to PCR make the procedure slow and expensive (Gobinda et al, supra).

Capture PCR (Lagerstrom M et al (1991) PCR Methods Applic 1:111–19) is a method for PCR amplification of DNA fragments adjacent to a known sequence in human and YAC DNA. As noted by Sarkar (supra), capture PCR also requires multiple restriction enzyme digestions and ligations to place an engineered double-stranded sequence into an unknown portion of the DNA molecule before PCR. Although the restriction and ligation reactions are carried out simultaneously, the requirements for extension, immobilization and two rounds of PCR and purification prior to sequencing render the method cumbersome and time consuming.

Parker J D et al (1991; Nucleic Acids Res 19:3055–60), teach walking PCR, a method for targeted gene walking which permits retrieval of unknown sequence. In this same vein, PROMOTERFINDER™ a new kit available from Clontech (Palo Alto Calif.) uses PCR and primers derived from p53 to walk in genomic DNA. Nested primers and special PromoterFinder libraries are used to detect upstream sequences such as promoters and regulatory elements. This process avoids the need to screen libraries and is useful in finding intron/exon junctions.

Another new PCR method, "*Improved Method for Obtaining Full Length cDNA Sequences*" by Guegler et al, patent application Ser. No. 08/487,112, filed Jun. 7, 1995 and hereby incorporated by reference, employs XL-PCR (Perkin-Elmer, Foster City Calif.) to amplify and extend partial nucleotide sequence into longer pieces of DNA. This method was developed to allow a single researcher to process multiple genes (up to 20 or more) at one time and to obtain an extended (possibly full-length) sequence within 6–10 days. This new method replaces methods which use labelled probes to screen plasmid libraries and allow one researcher to process only about 3–5 genes in 14–40 days.

In the first step, which can be performed in about two days, any two of a plurality of primers are designed and synthesized based on a known partial sequence. In the second step, which takes about six to eight hours, the sequence is extended by PCR amplification of a selected library. The third and fourth steps, which take about one day, are purification of the amplified cDNA and its ligation into an appropriate vector. The fifth step, which takes about one day, involves transforming and growing up host bacteria. The sixth step, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg Md.). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

A new method for analyzing either the size or the nucleotide sequence of PCR products is capillary electrophoresis. Systems for rapid sequencing are available from Perkin Elmer (Foster City Calif.), Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/Light intensity is converted to electrical signal using appropriate software (eg. GENOTYPER™ and SEQUENCE NAVIGATORS from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Another aspect of the subject invention is to provide for hjak2 hybridization probes which are capable of hybridizing with naturally occurring nucleotide sequences encoding HJAK2. The stringency of the hybridization conditions will determine whether the probe identifies only the native nucleotide sequence of hjak2 or sequences of other closely related Jak2 kinase molecules. If degenerate hjak2 nucleotide sequences of the subject invention are used for the detection of related kinase encoding sequences, they should preferably contain at least 50% of the nucleotides of the sequences presented herein. Hybridization probes of the subject invention may be derived from the nucleotide sequence presented in SEQ ID NO: 1 or from surrounding genomic sequences comprising untranslated regions such as promoters, enhancers and introns. Such hybridization probes may be labelled with appropriate reporter molecules.

Means for producing specific hybridization probes for this Jak2 kinase include oligolabelling, nick translation, end-labelling or PCR amplification using a labelled nucleotide.

Alternatively, the cDNA sequence may be cloned into a vector for the production of an mRNA probe.

Such vectors are known in the art, are commercially available, and may be used to synthesize RNA probes in vitro by addition of an appropriate RNA polymerase such as T7, T3 or SP6 and labeled nucleotides. A number of companies (such as Pharmacia Biotech, Piscataway N.J.; Promega, Madison Wis.; US Biochemical Corp, Cleveland, Ohio; etc.) supply commercial kits and protocols for these procedures.

It is also possible to produce a DNA sequence, or portions thereof, entirely by synthetic chemistry. Sometimes the source of information for producing this sequence comes from the known homologous sequence from closely related organisms. After synthesis, the nucleic acid sequence can be used alone or joined with a pre-existing sequence and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

Hjak2 nucleotide sequence can be used in a diagnostic test or assay to detect disorder or disease processes associated with abnormal expression of hjak2. The nucleotide sequence is added to a sample (fluid, cell or tissue) from a patient under hybridizing conditions. After an incubation period, the sample is washed with a compatible fluid which optionally contains a reporter molecule which will bind the specific nucleotide. After the compatible fluid is rinsed off, the reporter molecule is quantitated and compared with a standard for that fluid, cell or tissue. If hjak2 expression is significantly different from the standard, the assay indicates the presence of disorder or disease. The form of such qualitative or quantitative methods may include northern analysis, dot blot or other membrane-based technologies, dip stick, pin or chip technologies, PCR, ELISAs or other multiple sample format technologies.

This same assay, combining a sample with the nucleotide sequence, is applicable in evaluating the efficacy of a particular therapeutic treatment regime. It may be used in animal studies, in clinical trials, or in monitoring the treatment of an individual patient. First, standard expression must be established for use as a basis of comparison. Second, samples from the animals or patients affected by a disorder or disease are combined with the nucleotide sequence to evaluate the deviation from the standard or normal profile. Third, an entirely new or pre-existing therapeutic agent is administered, and a treatment profile is generated. This post-treatment assay is evaluated to determine whether the patient profile progresses toward or returns to the standard pattern. Successive treatment profiles may be used to show the efficacy of treatment over a period of several days or several months.

The nucleotide sequence for hjak2 can also be used to generate probes for mapping native genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of such genetic maps can regularly be found in the journal Science (eg, 1994; 265: 1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal and carrier or affected individuals.

The nucleotide sequence encoding HJAK2 may be used to produce an amino acid sequence using well known methods of recombinant DNA technology. Goeddel (1990, *Gene Expression Technology. Methods and Enzymology*, Vol 185, Academic Press, San Diego Calif.) is one among many publications which teach expression of an isolated, purified nucleotide sequence. The amino acid or peptide may be expressed in a variety of host cells, either prokaryotic or eukaryotic. Host cells may be from the same species from which the nucleotide sequence was derived or from a different species. Advantages of producing an amino acid sequence or peptide by recombinant DNA technology include obtaining adequate amounts for purification and the availability of simplified purification procedures.

Cells transformed with hjak2 nucleotide sequence may be cultured under conditions suitable for the expression and recovery of peptide from cell culture. The peptide produced by a recombinant cell may be secreted or may be contained intracellularly depending on the sequence and/or the vector used. In general, it is more convenient to prepare recombinant proteins in secreted form, and this is accomplished by ligating hjak2 to a recombinant nucleotide sequence which directs its movement through a particular prokaryotic or eukaryotic cell membrane. Other recombinant constructions may join hjak2 to nucleotide sequence encoding a polypeptide domain which will facilitate protein purification (Kroll D J et al (1993) DNA Cell Biol 12:441–53).

Direct peptide synthesis using solid-phase techniques (Creighton (1983) *Proteins Structures And Molecular Principles*, W H Freeman and Co, New York N.Y. pp. 50–60) is an alternative to recombinant or chimeric peptide production. Automated synthesis may be achieved, for example, an Applied Biosystems 431A peptide synthesizer in accordance with the instructions provided by the manufacturer. Additionally HJAK2 or any part thereof may be mutated during direct synthesis and combined using chemical methods with other kinase sequences, or parts thereof.

Although an amino acid sequence or oligopeptide used for antibody induction does not require biological activity, it must be immunogenic. HJAK2 used to induce specific antibodies may have an amino acid sequence consisting of at least five amino acids and preferably at least 10 amino acids. Short stretches of amino acid sequence may be fused with those of another protein such as keyhole limpet hemocyanin, and the chimeric peptide used for antibody production. Alternatively, the peptide may be of sufficient length to contain an entire domain.

Antibodies specific for HJAK2 may be produced by inoculation of an appropriate animal with an antigenic fragment of the peptide. An antibody is specific for HJAK2 if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi R et al (1989) PNAS 86:3833–3837, or Huse WD et al (1989) Science 256: 1275–1281), or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules which specifically bind HJAK2. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of HJAK2 active in normal, diseased, or therapeutically treated cells or tissues.

The examples below are provided to illustrate the subject invention. These examples are provided by way of illustration and are not included for the purpose of limiting the invention.

EXAMPLES

I Placenta cDNA Library Construction

The cDNA library was constructed from normal placenta. The tissue was lysed in a buffer containing guanidinium isothiocyanate. The lysate was extracted with phenol chloroform and precipitated with ethanol. Poly A+ RNA was isolated using biotinylated oligo d(T) primer and streptavidin coupled to a paramagnetic particle (Promega Corp. Madison Wis.) and sent to Stratagene (La Jolla Calif.) for cDNA library preparation. The cDNA synthesis was primed using both oligo d(T) and random hexamers, and the two cDNA libraries were treated separately. Synthetic adapter oligonucleotides were ligated onto the ends of the cDNAs which were digested with XhoI and inserted into the UNI-ZAP vector system (Stratagene).

The PBLUESCRIPT phagemid (Stratagene) was excised from each library, and phagemids from the two cDNA libraries were combined into a single library by mixing equal numbers of bacteriophage. The phagemids were transformed into *E. coli* host strain XLI-BLUE (Stratagene). Enzymes from both PBLUESCRIPT and a cotransformed f1 helper phage nicked the DNA, initiated new DNA synthesis, and created the smaller, single-stranded circular plasmid DNA molecules which contained the cDNA insert. The plasmid DNA was released, purified, and used to reinfect fresh host cells (SOLR, Stratagene). Presence of the β-lactamase gene on the plasmid allowed transformed bacteria to grow on medium containing ampicillin.

II Isolation of cDNA Clones

Plasmid DNAs containing the cDNA insert were purified using the QIAWELL-8 plasmid purification system from QIAGEN Inc (Chatsworth Calif.) according to standard protocol. The DNA was eluted and prepared for DNA sequencing and other analytical manipulations.

The cDNA inserts from random isolates of the placenta library were partially sequenced. The cDNAs were sequenced by the method of Sanger F and AR Coulson (1975; J Mol Biol 94:441f), using a CATALYST 800 or a MACROLAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and reading frame was determined.

III Sequencing of cDNA Clones

The cDNA inserts from random isolates of the placenta library were sequenced in part. Methods for DNA sequencing are well known in the art and employ such enzymes as the Klenow fragment of DNA polymerase I, SEQUENASE® (US Biochemical Corp., or Taq polymerase. Methods to extend the DNA from an oligonucleotide primer annealed to the DNA template of interest have been developed for both single- and double-stranded templates. Chain termination reaction products were separated using electrophoresis and detected via their incorporated, labelled precursors. Recent improvements in mechanized reaction preparation, sequencing and analysis have permitted expansion in the number of sequences that can be determined per day. Preferably, the process is automated with machines such as the MICROLAB 2200 (Hamilton, Reno Nev.), Peltier thermal cycler (PTC200; MJ Research, Watertown Mass.) and the Applied Biosystems Catalyst 800 and 377 and 373 DNA sequencers.

The quality of any particular cDNA library may be determined by performing a pilot scale analysis of the cDNAs and checking for percentages of clones containing vector, lambda or *E. coli* DNA, mitochondrial or repetitive DNA, and clones with exact or homologous matches to public databases. The number of unique sequences, those having no known match in any available database, are then recorded.

IV Homology Searching of cDNA Clones and Their Deduced Proteins

Each sequence so obtained was compared to sequences in GenBank using a search algorithm developed by Applied Biosystems and incorporated into the INHERIT 670 sequence analysis system. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul SF (1993) J Mol Evol 36:290–300; Altschul, SF et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. While it is useful for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

The partial hjak2 molecule presented and claimed in this application was identified using the criteria above. The full length nucleic and amino acid sequences for this novel human Jak2 kinase are shown in FIGS. 1A, 1B, 1C, 1D, 1E, 1F, 1G, and 1H.

Figure 2A:
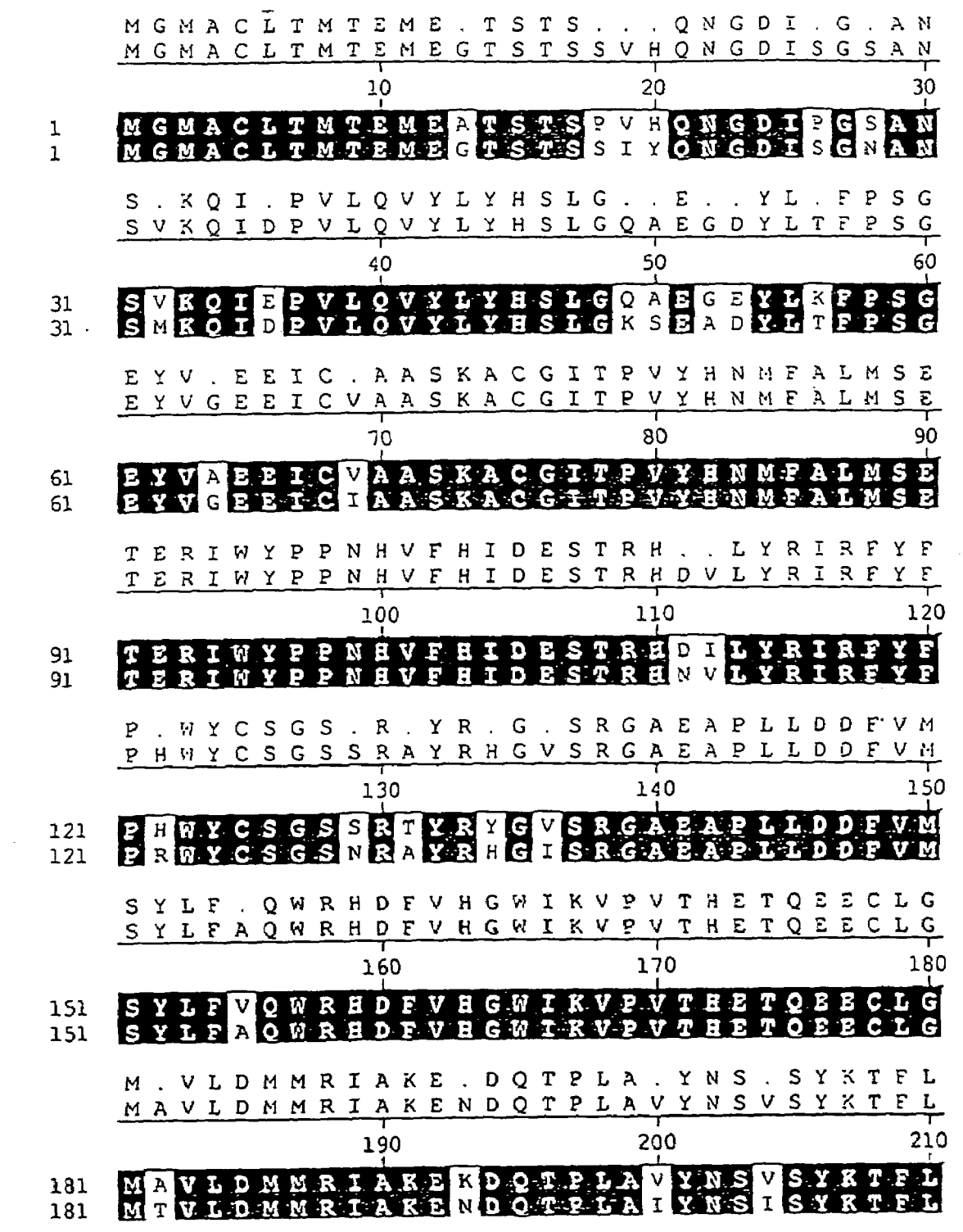
Figure 2B:
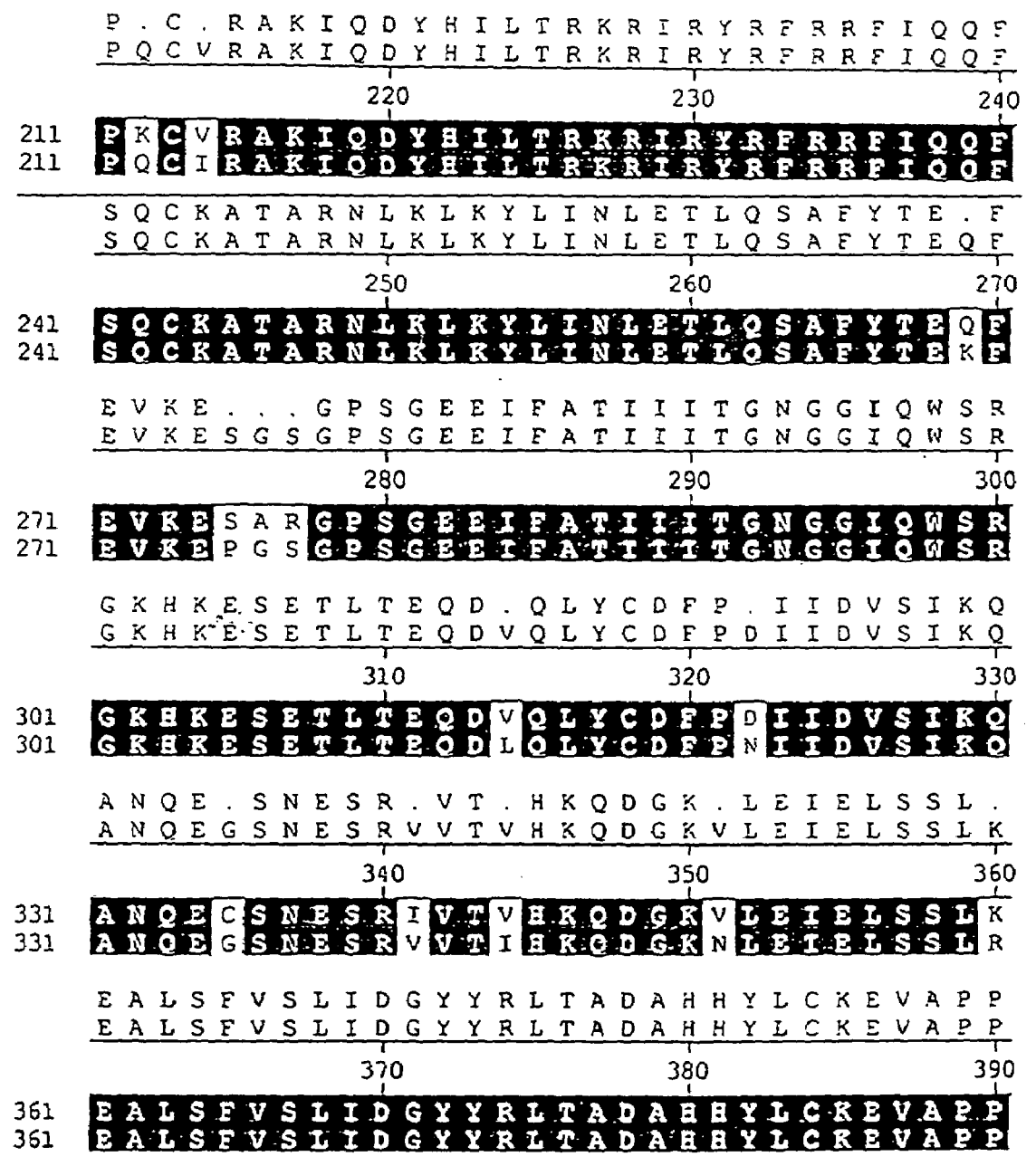
Figure 2C:
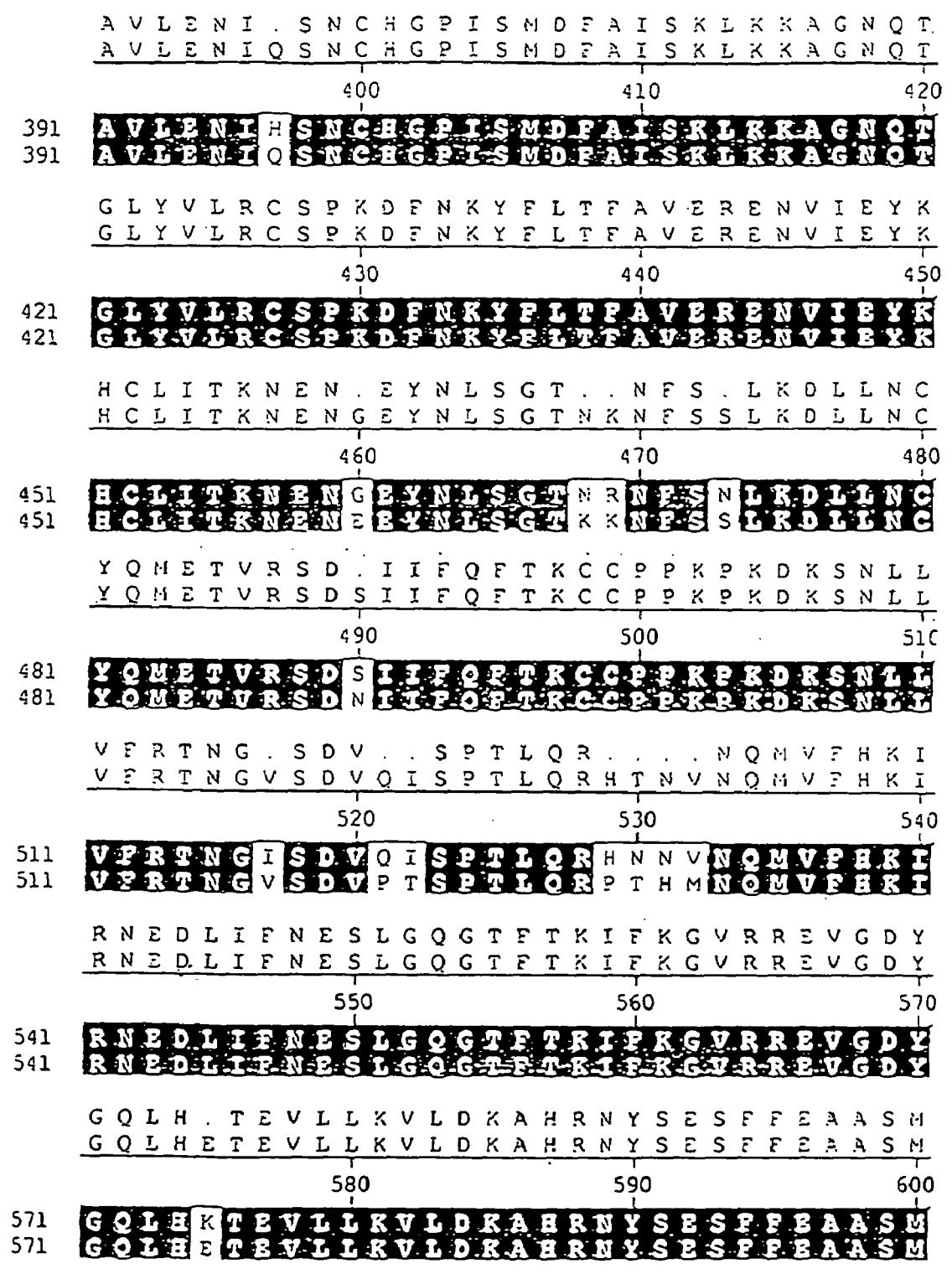
Figure 2D:
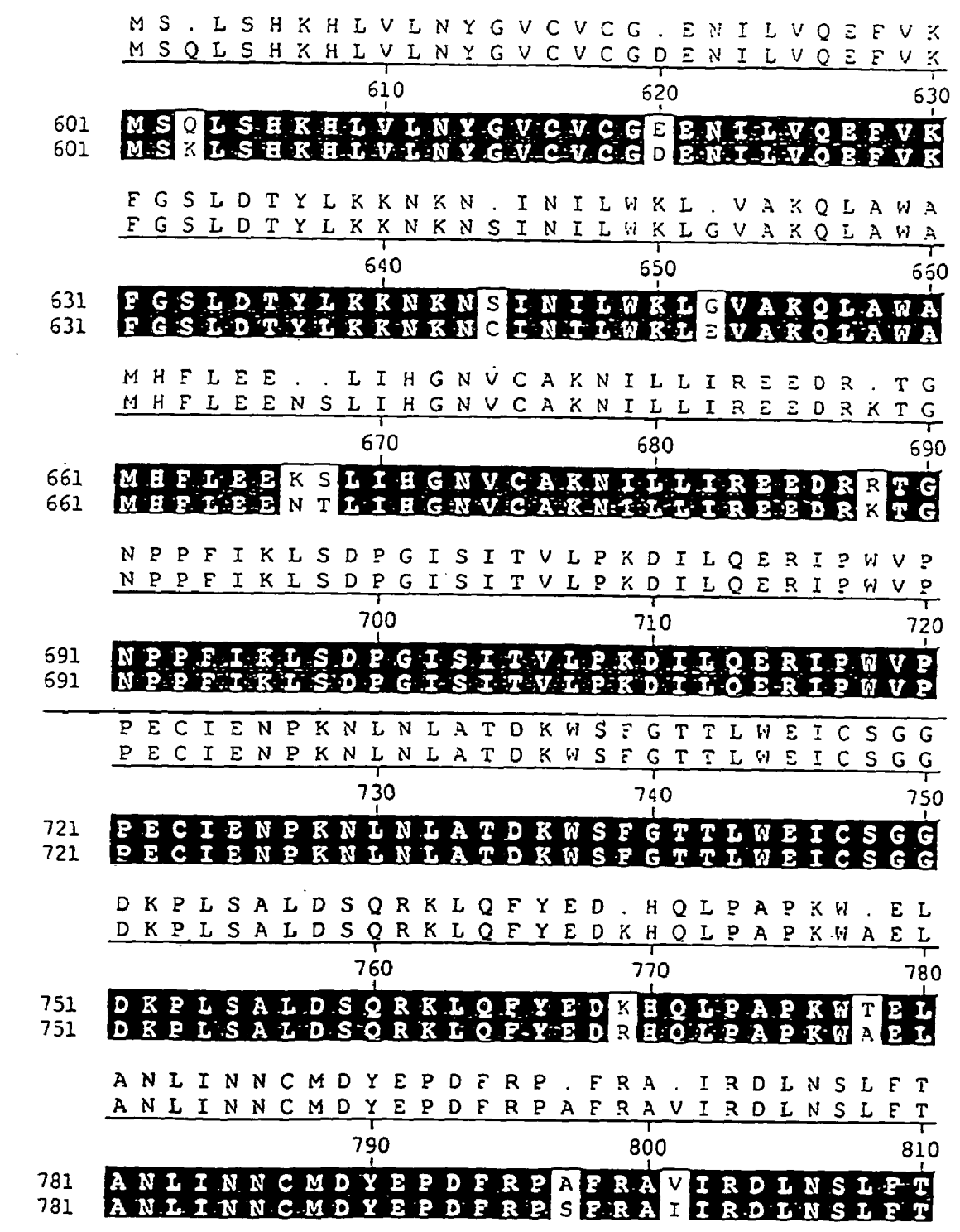
Figure 2E:
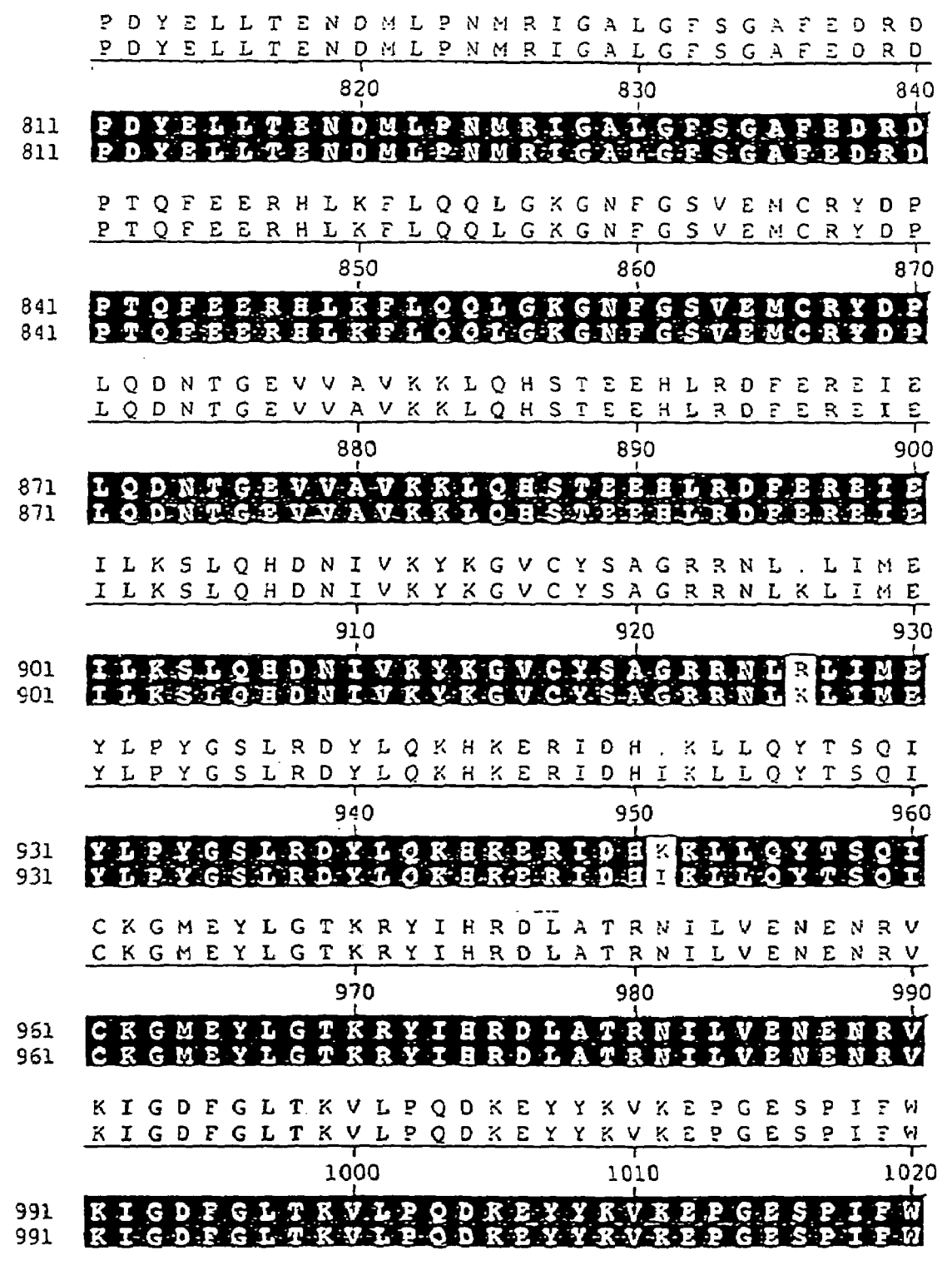
Figure 2F:
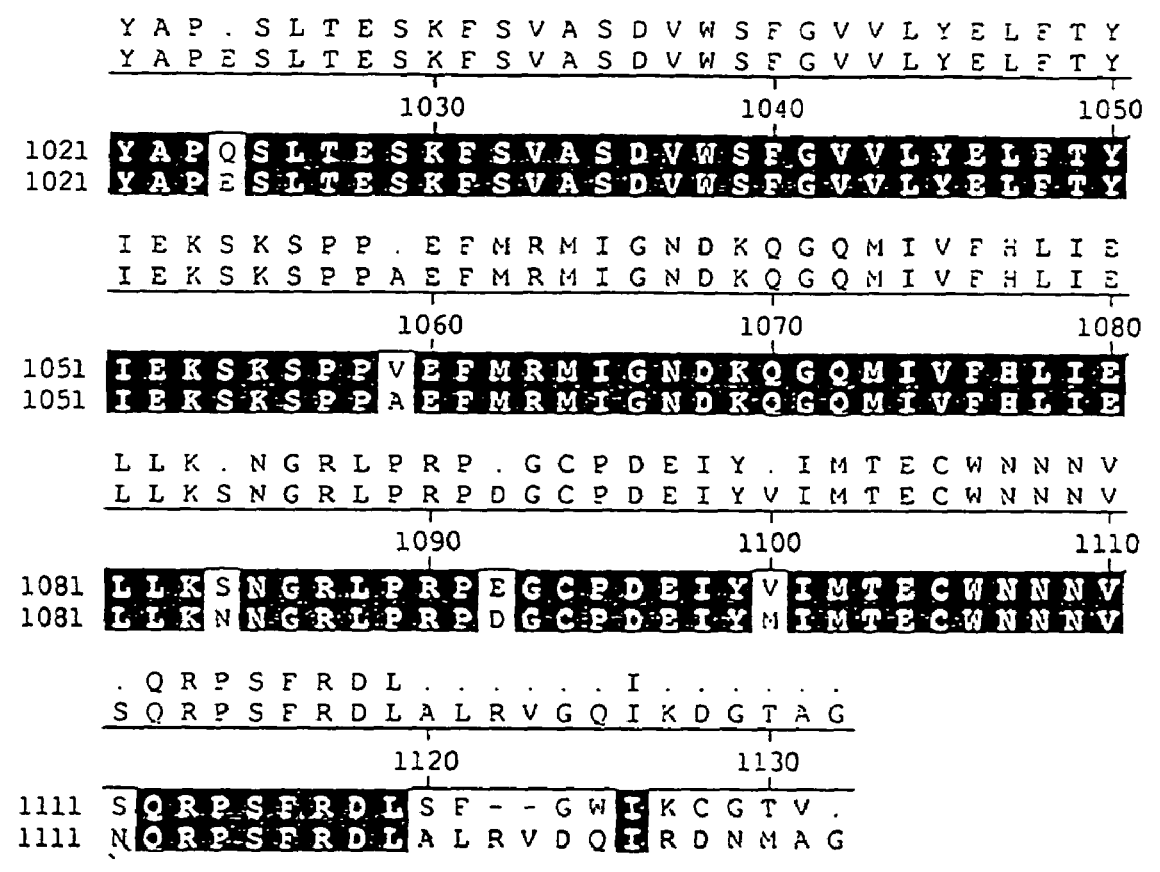

FIGS. 2A, 2B, 2C, 2D, and 2E shows the alignment between the translated amino acid sequence for hjak2 and the closest related molecule, murine Jak2 kinase (MUSPTK1; GenBank GI 409584; Wilks AF (1989) Proc Nat Acad Sci 86:1603–7).

V Extension of cDNAs to Full Length

The partial sequence originally identified in Incyte Clone 179527 was used to design oligonucleotide primers for extension of the cDNAs to full length. Primers are designed based on known sequence; one primer is synthesized to initiate extension in the antisense direction (XLF) and the other to extend sequence in the sense direction (XLF). The primers allow the sequence to be extended "outward" generating amplicons containing new, unknown nucleotide sequence for the gene of interest. The primers may be designed using OLIGO 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations was avoided.

The placenta cDNA library was used with "XLR=GGGCGGAAGTGCTCTCGGCGGAAG" with --XLR (SEQ ID NO:4) and "XLF=AGTGTGCTACAGTGCTGGTCGTCG" with --XLF (SEQ ID NO:5) primers to extend and amplify Incyte Clone 179527 to obtain the full length Jak2 kinase sequence.

By following the instructions for the XL-PCR kit and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Although all extensions potentially contain a full length gene, some of the largest products or bands are selected and cut out of the gel. Further purification involves using a commercial gel extraction method such as QIAQUICK (QIAGEN Inc). After recovery of the DNA, Klenow enzyme is used to trim single-stranded, nucleotide overhangs creating blunt ends which facilitate religation and cloning.

After ethanol precipitation, the products are redissolved in 13 µl of ligation buffer. Then, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, 12 colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 40° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Diagnostic Assay Using Hjak2 Specific Oligomers

In those cases where a specific condition (see definitions, supra) is suspected to involve expression of altered quantities of hjak2, oligomers may be designed to establish the presence and/or quantity of mRNA expressed in a biological sample. There are several methods currently being used to quantitate the expression of a particular molecule. Most of these methods use radiolabelled (Melby P C et al 1993 J Immunol Methods 159:235–44) or biotinylated (Duplaa C et al 1993 Anal Biochem 212:229–236) nucleotides, coamplification of a control nucleic acid, and standard curves onto which the experimental results are interpolated. Quantitation may be speeded up by running the assay in an ELISA format where the oligomer-of-interest is presented in various dilutions and a colorimetric response gives rapid quantitation. For example, a complete HJAK2 deficiency may result in the inability to undergo cell division or to react to an infectious organism. In like manner, overexpression may cause major inflammation, swelling and major tissue damage. In either case, a quick diagnosis may allow health professionals to treat the condition and prevent worsening of the condition. This same assay can be used to monitor progress of the patient as his/her physiological situation moves toward the normal range during therapy.

VII Sense or Antisense Molecules

Knowledge of the correct cDNA sequence of this Jak2 kinase or its regulatory elements enable its use as a tool in sense (Youssoufian H and H F Lodish 1993) Mol Cell Biol 13:98–104) or antisense (Eguchi et al (1991) Annu Rev Biochem 60:631–652) technologies for the investigation or alteration of gene expression. To inhibit in vivo or in vitro hjak2 expression, an oligonucleotide based on the coding sequence of an hjak2 designed with OLIGO 4.0 software (National Biosciences Inc) is used. Alternatively, a fragment of an hjak2 is produced by digesting hjak2 coding sequence with restriction enzymes. These enzymes and specific restrictions sites may be selected using INHERIT analysis software (Applied Biosystems), and the strands separated by heating the fragments and selecting for the antisense strand. Either the oligonucleotide or the fragment may be used to inhibit hjak2 expression. Furthermore, antisense molecules can be designed to inhibit promoter binding in the upstream nontranslated leader or at various sites along the hjak2 coding region. Alternatively, antisense molecules may be designed to inhibit translation of an mRNA into polypeptide by preparing an oligomer or fragment which will bind in the region spanning approximately −10 to +10 nucleotides at the 5′ end of the coding sequence. These technologies are now well known to those of in the art.

In addition to using antisense molecules constructed to interrupt transcription of the open reading frame, modifications of gene expression can be obtained by designing antisense sequences to enhancers, introns, or even to trans-acting regulatory genes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Any of these types of antisense molecules may be placed in expression vectors and used to transform preferred cells or tissues. This may include introduction of the expression vector into a organ, tumor, synovial cavity or the vascular system for transient or short term therapy or introduction via gene therapy technologies for long term treatment. Transient expression may last for a month or more with a nonreplicating vector and three months or more if appropriate replication elements are used in the transformation or expression system.

Stable transformation of appropriate dividing cells with a vector containing the antisense molecule can produce a transgenic cell line, tissue or organism (see, for example, Trends in Biotechnol 11:155–215 (1993) and U.S. Pat. No. 4,736,866, 12 Apr. 1988). Those cells which assimilate or replicate enough copies of the vector to allow stable integration will also produce enough antisense molecules to compromise or entirely eliminate normal activity of the hjak2. Frequently, the function of an hjak2 can be ascertained by observing behaviors such as lethality, loss of a physiological pathway, changes in morphology, etc. at the cellular, tissue or organismal level.

VIII Expression of HJAK2

Expression of the HJAK2 may be accomplished by subcloning the cDNA into appropriate vectors and transfecting the vectors into host cells. In this case, the cloning vector previously used for the generation of the tissue library also provides for direct expression of the hjak2 sequence in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods will produce a fusion protein corresponding to the first seven residues of β-galactosidase, about 5 to 15 residues which correspond to linker, and the peptide encoded within the hjak2 cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide linkers containing cloning sites as well as a stretch of DNA sufficient to hybridize to the end of the target cDNA (25 bases) can be synthesized chemically by standard methods. These primers can then used to amplify the desired gene fragments by PCR. The resulting fragments can be digested with appropriate restriction enzymes under standard conditions and isolated by gel electrophoresis. Alternatively, similar gene fragments can be produced by digestion of the cDNA with appropriate restriction enzymes and filling in the missing gene sequence with chemically synthesized oligonucleotides. Partial nucleotide sequence from more than one kinase homolog can be ligated together and cloned into appropriate vectors to optimize expression.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

If native promoters are not part of the cDNA, other host specific promoters may be specifically combined with the coding region of hjak2. They include MMTV, SV40, and metallothionein promoters for CHO cells; trp, lac, tac and T7 promoters for bacterial hosts; and alpha factor, alcohol oxidase and PGH promoters for yeast. In addition, transcription enhancers, such as the rous sarcoma virus (RSV) enhancer, may be used in mammalian host cells. Once homogeneous cultures of recombinant cells are obtained through standard culture methods, large quantities of recombinantly produced peptide can be recovered from the conditioned medium and analyzed using methods known in the art.

Ix Isolation of Recombinant HJAK2

HJAK2 may be expressed as a recombinant protein with one or more additional polypeptide domains added to facilitate protein purification.

Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen) between the purification domain and the hjak2 sequence may be useful to facilitate expression of HJAK2.

X Testing HJAK2 Activity

The sequence for HJAK2 in this application present many different domains (and subdomains as detailed in the background of the invention) which may be utilized: 1) individually for the production of antibodies, 2) in functional groups (eg. to span a membrane), and 3) as interchangeable, usable parts of a chimeric kinase. For example, a known, full length kinase such as the hjak2 kinase of this application may be used to swap related portions of the nucleic acid sequence, analogous to domains or subdomains of MAP kinase polypeptides. The chimeric nucleotides, so produced, may be introduced into prokaryotic host cells (as reviewed in Strosberg A D and Marullo S (1992) Trends Pharma Sci 13:95–98) or eukaryotic host cells. These host cells are then employed in procedures to determine what molecules activate the kinase or what molecules are activated by a kinase. Such activating or activated molecules may be of extracellular, intracellular, biologic or chemical origin.

An example of a test system, in this case for hjak2 kinase, can be based on the interaction of protein tyrosine kinases with chemokine receptors (Taniguchi T (1995) Science 268:251–255). These receptors are capable of activating a variety of nonreceptor protein tyrosine kinases when stimulated by an extracellular chemokine. C—X—C chemokines such as platelet factor 4, interleukin-8, connective tissue activating protein III, neutrophil activating peptide 2, are soluble activators of neutrophils.

A standard measure of neutrophil activation involves measuring the mobilization of $Ca^{++}$ as part of the signal transduction pathway. The experiment involves several steps. First, blood cells obtained from venipuncture are fractionated by centrifugation on density gradients. Enriched populations of neutrophils are further fractionated on columns by negative selection using antibodies specific for other blood cells types. Next, neutrophils are transformed with an expression vector containing the kinase nucleic acid sequence of interest and preloaded fluorescent probe whose emission characteristics have been altered by $Ca^{++}$ binding. Or in the alternative, the neutrophil is preloaded with the purified kinase of interest and fluorescent probe. Then, when the cells are exposed to an appropriate chemokine, the chemokine receptor activates the kinase which, in turn, initiates $Ca^{++}$ flux. $Ca^{++}$ mobilization is observed and measured using fluorometry as has been described in Grynkievicz G et al (1985) J Biol Chem 260:3440, and McColl S et al (1993) J Immunol 150:4550–4555, incorporated herein by reference.

XI Identification of or Production of HJAK2 Specific Antibodies

Purified HJAK2 is used to screen a pre-existing antibody library or to raise antibodies using either polyclonal or monoclonal methodology. In a polyclonal approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In a monoclonal approach, the amino acid sequence of HJAK2, as deduced from translation of the cDNA, is analyzed to determine regions of high immunogenicity. Oligopeptides comprising appropriate hydrophilic regions, as shown in FIG. 3, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled HJAK2 to identify those fusions producing the monoclonal antibody with the desired specificity. In a typical protocol, wells of plates (FAST; Becton-Dickinson, Palo Alto, Calif.) are coated with affinity purified, specific rabbit-anti-mouse antibodies (or suitable antispecies Ig) at 10 mg/ml. The coated wells are blocked with 1% BSA, washed and exposed to supernatants from hybridomas. After incubation the wells are exposed to labeled HJAK2, 1 mg/ml. Clones producing antibodies will bind a quantity of labeled HJAK2 which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$/M, preferably $10^9$ to $10^{10}$ or stronger, will typically be made by standard procedures as described in Harlow and Lane (1988) *Antibodies: A Laboratory Manual*, Cold Spring Harbor Laboratory, Cold Spring Harbor N.Y.; and in Goding (1986) *Monoclonal Antibodies: Principles and Practice*, Academic Press, New York City, both incorporated herein by reference.

XII Diagnostic Test Using HJAK2 Specific Antibodies

Particular HJAK2 antibodies are useful for the diagnosis of prepathologic conditions, and chronic or acute diseases which are characterized by differences in the amount or distribution of HJAK2. To date, HJAK2 has been found only in the placenta library; however, its activity there is most probably associated with organ function, inflammation or defense.

Diagnostic tests for HJAK2 include methods utilizing the antibody and a label to detect HJAK2 in human body fluids, tissues or extracts of such tissues. The polypeptides and antibodies of the present invention may be used with or without modification. Frequently, the polypeptides and antibodies will be labeled by joining them, either covalently or noncovalently, with a reporter molecule. A wide variety of labels and conjugation techniques are known and have been reported extensively in both the scientific and patent literature. Suitable reporter molecules or labels include those radionuclides, enzymes, fluorescent, chemiluminescent, or chromogenic agents previously mentioned as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound HJAK2, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HJAK2 is preferred, but a competitive binding assay may be employed. These assays are described, among other places, in Maddox, D E et al (1983, J Exp Med 158:1211).

XIII Purification of Native HJAK2 Using Specific Antibodies

Native or recombinant HJAK2 can be purified by immunoaffinity chromatography using antibodies specific for that particular HJAK2. In general, an immunoaffinity column is constructed by covalently coupling the anti-HJAK2 antibody to an activated chromatographic resin.

Polyclonal immunoglobulins are prepared from immune sera either by precipitation with ammonium sulfate or by purification on immobilized Protein A (Pharmacia Biotech). Likewise, monoclonal antibodies are prepared from mouse ascites fluid by ammonium sulfate precipitation or chromatography on immobilized Protein A. Partially purified immunoglobulin is covalently attached to a chromatographic resin such as CNBr-activated SEPHAROSE (Pharmacia Biotech). The antibody is coupled to the resin, the resin is blocked, and the derivative resin is washed according to the manufacturer's instructions.

Such immunoaffinity columns may be utilized in the purification of HJAK2 by preparing a fraction from cells containing HJAK2 in a soluble-form. This preparation may be derived by solubilization of whole cells or of a subcellular fraction obtained via differential centrifugation (with or without addition of detergent) or by other methods well known in the art. Alternatively, soluble HJAK2 containing a signal sequence may be secreted in useful quantity into the medium in which the cells are grown.

A soluble HJAK2-containing preparation is passed over the immunoaffinity column, and the column is washed under conditions that allow the preferential absorbance of HJAK2 (eg, high ionic strength buffers in the presence of detergent). Then, the column is eluted under conditions that disrupt antibody/HJAK2 binding (eg, a buffer of pH 2–3 or a high concentration of a chaotrope such as urea or thiocyanate ion), and HJAK2 is collected.

XIV Drug Screening

This invention is particularly useful for screening therapeutic compounds by using binding fragments of HJAK2 in any of a variety of drug screening techniques. The peptide fragment employed in such a test may either be free in solution, affixed to a solid support, borne on a cell surface or located intracellularly. One may measure, for example, the formation of complexes between HJAK2 and the agent being tested.

Alternatively, one can examine the diminution in complex formation between HJAK2 and a receptor caused by the agent being tested.

Methods of screening for drugs or any other agents which can affect macrophage activation comprise contacting such an agent with HJAK2 fragment and assaying for the presence of a complex between the agent and the HJAK2 fragment. In such assays, the HJAK2 fragment is typically labelled. After suitable incubation, free HJAK2 fragment is separated from that present in bound form, and the amount of free or uncomplexed label is a measure of the ability of the particular agent to bind to HJAK2.

Another technique for drug screening provides high throughput screening for compounds having suitable binding affinity to the HJAK2 polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with HJAK2 fragment and washed. Bound HJAK2 fragment is then detected by methods well known in the art. Purified HJAK2 can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding HJAK2 specifically compete with a test compound for binding to HJAK2 fragments. In this manner, the antibodies can be used to detect the presence of any peptide which shares one or more antigenic determinants with HJAK2.

XV Identification of Molecules Which Interact with HJAK2

The inventive purified HJAK2 is a research tool for identification, characterization and purification of interacting molecules. Appropriate labels are incorporated into HJAK2 by various methods known in the art and HJAK2 is used to capture soluble or interact with membrane-bound molecules.

A preferred method involves labeling the primary amino groups in HJAK2 with $^{125}$I Bolton-Hunter reagent (Bolton, AE and Hunter, W M (1973) Biochem J 133: 529). This reagent has been used to label various molecules without concomitant loss of biological activity (Hebert Calif. et al (1991) J Biol Chem 266: 18989–94; McColl S et al (1993) J Immunol 150:4550–4555). Membrane-bound molecules are incubated with the labelled HJAK2 molecules, washed to removed unbound molecules, and the HJAK2 complex is quantified. Data obtained using different concentrations of HJAK2 are used to calculate values for the number, affinity, and association of HJAK2.

Labelled HJAK2 fragments are also useful as a reagent for the purification of molecules with which HJAK2 interacts, specifically including inhibitors. In one embodiment of affinity purification, HJAK2 is covalently coupled to a chromatography column. Cells and their membranes are extracted, HJAK2 is removed and various HJAK2-free subcomponents are passed over the column. Molecules bind to the column by virtue of their HJAK2 affinity. The HJAK2-complex is recovered from the column, dissociated and the recovered molecule is subjected to N-terminal protein sequencing or other identification procedure. If the captured molecule has an amino acid sequence, it can be used to design degenerate oligomers for use in cloning the gene from an appropriate cDNA library.

In an alternate method, monoclonal antibodies raised against HJAK2 fragments are screened to identify those which inhibit the binding of labelled HJAK2. These monoclonal antibodies are then used in affinity purification or expression cloning of associated molecules. Other soluble binding molecules are identified in a similar manner. Labelled HJAK2 is incubated with extracts or other appropriate materials derived from lung, kidney or other tissues with activated monocytes or macrophages. After incubation, HJAK2 complexes (which are larger than the lone HJAK2 fragment) are identified by a sizing technique such as size exclusion chromatography or density gradient centrifugation and are purified by methods well known in the art. The soluble binding protein(s) are subjected to N-terminal sequencing to obtain information sufficient for database identification, if the soluble protein is known, or for cloning, if the soluble protein is unknown.

XVI Use and Administration of Antibodies or Inhibitors to HJAK2

The antibodies and inhibitors can provide different effects when administered therapeutically. The antibodies and inhibitors are used to lessen or eliminate undue damage caused by disorders or diseases associated with upregulated HJAK2 expression. Each of these molecules or treatments (TSTs) will be formulated in a nontoxic, inert, pharmaceutically acceptable aqueous carrier medium preferably at a pH of about 5 to 8, more preferably 6 to 8, although the pH may vary according to the different characteristics of the peptide, antibody or inhibitor being formulated and the condition to be treated. Characteristics of TSTs include solubility of the molecule, half-life, antigenicity/immunogenicity and the ability of the inhibitor to reach its target(s). These and other characteristics may aid in defining an effective carrier. Native human proteins are preferred as TSTs, but recombinant peptides as well as organic or synthetic molecules resulting from drug screens may be equally effective in particular situations.

TSTs may be delivered by known routes of administration including but not limited to topical creams and gels; transmucosal spray and aerosol; transdermal patch and bandage;

injectable, intravenous and lavage formulations; and orally administered liquids and pills particularly formulated to resist stomach acid and enzymes. The particular formulation, exact dosage, and route of administration will be determined by the attending physician and will vary according to each specific situation. Such determinations are made by considering multiple variables such as the condition to be treated, the TST to be administered, and the pharmacokinetic profile of the particular TST. Additional factors which may be taken into account include disease state (eg. severity) of the patient, age, weight, gender, diet, time and frequency of administration, drug combination, reaction sensitivities, and tolerance/response to therapy. Long acting TST formulations might be administered every 3 to 4 days, every week; or once every two weeks depending on half-life and clearance rate of the particular TST.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for different TSTs. Administration to lung cells may necessitate delivery in a manner different from that to kidney or other cells.

It is contemplated that conditions associated with altered HJAK2 expression are treatable with TSTs. These conditions, which specifically include, but are not limited to, anemia, arteriosclerosis, asthma, bronchitis, emphysema, gingivitis, inflammatory bowel disease, insulin-dependent diabetes mellitus, leukemia, multiple endocrine neoplasias, osteoarthritis, osteoporosis, pulmonary fibrosis, rheumatoid arthritis, septic shock syndromes, and systemic lupus erythematosus may be specifically diagnosed by the tests discussed above. In addition, such tests may be used to monitor treatment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

The invention claimed is:

1. An isolated polynucleotide encoding a polypeptide selected from the group consisting of:
   a) the amino acid sequence of SEQ ID NO:2, and
   b) a fragment of the amino acid sequence of SEQ ID NO:2, wherein said fragment has kinase activity.

2. An isolated polynucleotide of claim 1 which encodes a polypeptide comprising the amino acid sequence of SEQ ID NO:2.

3. An isolated polynucleotide of claim 1 which encodes a polypeptide comprising a fragment of an amino acid sequence of SEQ ID NO:2, wherein said fragment has kinase activity.

4. A recombinant polynucleotide comprising a promoter sequence operably linked to a polynucleotide of claim 1.

5. An isolated transformed with a recombinant polynucleotide of claim 4.

6. A method for producing a polypeptide encoded by the polynucleotide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide of claim 1, and
   b) recovering the polypeptide so expressed.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 4482 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: Placenta
      (B) CLONE: 179527

(xi) SEQUENCE DESCRIPTION: SEQ ID NO:1:

```
CCACGCGTCC GGTTGCCAAC CCGCAGGCGA CTGGGCGCTT CATCCCACCC TCACCCCTTT      60

CCAGCCAAGG TGGCTGATCG GAGTCAGGCT CTCGAGGTCG CATTGCCACG AAACGGNGTG     120

TGTGAGCGCG TTGTCCCCGG NCCCCGGGGC CACTTCCCCT CGGCCTAGNA GACTGGACTG     180

GGGAAGGACG GGTCTGTTGT ACCCGGGAGG TGGAAGGAAA AGCCGAAAGC GGAGAAGTGT     240

GCGGGAGGGG AGTCTCCGCG CGGAGGNAGA CCGGNCTCCT CCAGTGCAGG TTGTGCGCTG     300

GGGAGCCAGC CASGGCAAAT GTTCTGAAAA AGACTCTGCA TGGGAATGGC CTGCCTTACG     360

ATGACAGAAA TGGAGGGAAC ATCCACCTCT TCTATATATC AGAATGGTGA TATTTCTGGA     420

AATGCCAATT CTATGAAGCA AATAGATCCA GTTCTTCAGG TGTATCTTTA CCATTCCCTT     480

GGGAAATCTG AGGCAGATTA TCTGACCTTT CCATCTGGGG AGTATGTTGG AGAAGAAATC     540

TGTATTGCTG CTTCTAAAGC TTGTGGTATC ACACCTGTGT ATCATAATAT GTTTGCTTTA     600

ATGAGTGAAA CAGAAAGGAT CTGGTATCCA CCCAACCATG TCTTCCATAT AGATGAGTCA     660

ACCAGGCATA ATGTACTCTA CAGAATAAGA TTTTACTTTC CTCGTTGGTA TTGCAGTGGC     720
```

```
AGCAACAGAG CCTATCGGCA TGGAATATCT CGAGGTGCTG AAGCTCCTCT TCTTGATGAC    780
TTTGTCATGT CTTACCTCTT TGCTCAGTGG CGGCATGATT TTGTGCATGG ATGGATAAAA    840
GTACCTGTGA CTCATGAAAC ACAGGAAGAA TGTCTTGGGA TGACAGTGTT AGATATGATG    900
AGAATAGCCA AGAAAACGA TCAAACCCCA CTGGCCATCT ATAACTCTAT CAGCTACAAG    960
ACATTCTTAC CACAATGTAT TCGAGCAAAG ATCCAAGACT ATCATATTTT GACAAGGAAG   1020
CGAATAAGGT ACAGATTTCG CAGATTTATT CAGCAATTCA GCCAATGCAA AGCCACTGCC   1080
AGAAACTTGA AACTTAAGTA TCTTATAAAT CTGGAAACTC TGCAGTCTGC CTTCTACACA   1140
GAGAAATTTG AAGTAAAAGA ACCTGGAAGT GGTCCTTCAG GTGAGGAGAT TTTTGCAACC   1200
ATTATAATAA CTGGAAACGG TGGAATTCAG TGGTCAAGAG GGAAACATAA AGAAAGTGAG   1260
ACACTGACAG AACAGGATTT ACAGTTATAT TGCGATTTTC CTAATATTAT TGATGTCAGT   1320
ATTAAGCAAG CAAACCAAGA GGGTTCAAAT GAAAGCCGAG TTGTAACTAT CCATAAGCAA   1380
GATGGTAAAA ATCTGGAAAT TGAACTTAGC TCATTAAGGG AAGCTTGTC TTTCGTGTCA    1440
TTAATTGATG GATATTATAG ATTAACTGCA GATGCACATC ATTACCTCTG TAAAGAAGTA   1500
GCACCTCCAG CCGTGCTTGA AAATATACAA AGCAACTGTC ATGGCCCAAT TTCGATGGAT   1560
TTTGCCATTA GTAAACTGAA GAAAGCAGGT AATCAGACTG GACTGTATGT ACTTCGATGC   1620
AGTCCTAAGG ACTTTAATAA ATATTTTTTG ACTTTTGCTG TCGAGCGAGA AAATGTCATT   1680
GAATATAAAC ACTGTTTGAT TACAAAAAAT GAGAATGAAG AGTACAACCT CAGTGGGACA   1740
AAGAAGAACT TCAGCAGTCT TAAAGATCTT TTGAATTGTT ACCAGATGGA AACTGTTCGC   1800
TCAGACAATA TAATTTTCCA GTTTACTAAA TGCTGTCCCC CAAAGCCAAA AGATAAATCA   1860
AACCTTCTAG TCTTCAGAAC GAATGGTGTT TCTGATGTAC CAACCTCACC AACATTACAG   1920
AGGCCTACTC ATATGAACCA AATGGTGTTT CACAAAATCA GAAATGAAGA TTTGATATTT   1980
AATGAAAGCC TTGGCCAAGG CACTTTTACA AAGATTTTTA AAGGCGTACG AAGAGAAGTA   2040
GGAGACTACG GTCAACTGCA TGAAACAGAA GTTCTTTTAA AAGTTCTGGA TAAAGCACAC   2100
AGGAACTATT CAGAGTCTTT CTTTGAAGCA GCAAGTATGA TGAGCAAGCT TTCTCACAAG   2160
CATTTGGTTT TAAATTATGG AGTATGTGTC TGTGGAGACG AGAATATTCT GGTTCAGGAG   2220
TTTGTAAAAT TTGGATCACT AGATACATAT CTGAAAAAGA ATAAAAATTG TATAAATATA   2280
TTATGGAAAC TTGAAGTTGC TAAACAGTTG GCATGGGCCA TGCATTTTCT AGAAGAAAAC   2340
ACCCTTATTC ATGGGAATGT ATGTGCCAAA AATATTCTGC TTATCAGAGA AGAAGACAGG   2400
AAGACAGGAA ATCCTCCTTT CATCAAACTT AGTGATCCTG GCATTAGTAT TACAGTTTTG   2460
CCAAAGGACA TTCTTCAGGA GAGAATACCA TGGGTACCAC CTGAATGCAT TGAAAATCCT   2520
AAAAATTTAA ATTTGGCAAC AGACAAATGG AGTTTTGGTA CCACTTTGTG GGAAATCTGC   2580
AGTGGAGGAG ATAAACCTCT AAGTGCTCTG GATTCTCAAA GAAAGCTACA ATTTTATGAA   2640
GATAGGCATC AGCTTCCTGC ACCAAAGTGG GCAGAATTAG CAAACCTTAT AAATAATTGT   2700
ATGGATTATG AACCAGATTT CAGGCCTTCT TTCAGAGCCA TCATACGAGA TCTTAACAGT   2760
TTGTTTACTC CAGATTATGA ACTATTAACA GAAAATGACA TGTTACCAAA TATGAGGATA   2820
GGTGCCTTGG GGTTTTCTGG TGCCTTTGAA GACCGGGATC CTACACAGTT TGAAGAGAGA   2880
CATTTGAAAT TTCTACAGCA ACTTGGCAAG GGTAATTTTG GGAGTGTGGA GATGTGCCGG   2940
TATGACCCTC TACAGGACAA CACTGGGGAG GTGGTCGCTG TAAAAAAGCT TCAGCATAGT   3000
ACTGAAGAGC ACCTAAGAGA CTTTGAAAGG GAAATTGAAA TCCTGAAATC CCTACAGCAT   3060
```

-continued

```
GACAACATTG TAAAGTACAA GGGAGTGTGC TACAGTGCTG GTCGGCGTAA TCTAAAATTA    3120

ATTATGGAAT ATTTACCATA TGGAAGTTTA CGAGACTATC TTCAAAAACA TAAAGAACGG    3180

ATAGATCACA TAAAACTTCT GCAGTACACA TCTCAGATAT GCAAGGGTAT GGAGTATCTT    3240

GGTACAAAAA GGTATATCCA CAGGGATCTG GCAACGAGAA ATATATTGGT GGAGAACGAG    3300

AACAGAGTTA AAATTGGRGA TTTTGGGTTA ACCAAAGTCT TGCCACAAGA CAAAGAATAC    3360

TATAAAGTAA AAGAACCTGG TGAAAGTCCC ATATTCTGGT ATGCTCCAGA ATCACTGACA    3420

GAGAGCAAGT TTTCTGTGGC CTCAGATGTT TGGAGCTTTG GAGTGGTTCT GTATGAACTT    3480

TTCACATACA TTGAGAAGAG TAAAAGTCCA CCAGCGGAAT TTATGCGTAT GATTGGCAAT    3540

GACAAACAAG GACAGATGAT CGTGTTCCAT TTGATAGAAC TTTTGAAGAA TAATGGAAGA    3600

TTACCAAGAC CAGATGGATG CCCAGATGAG ATCTATATGA TCATGACAGA ATGCTGGAAC    3660

AATAATGTAA ATCAACGCCC CTCCTTTAGG GATCTAGCTC TTCGAGTGGA TCAAATAAGG    3720

GATAACATGG CTGGATGAAA GAAATGACCT TCATTCTGAG ACCAAAGTAG ATTTACAGAA    3780

CAAAGTTTTA TATTTCACAT TGCTGTGGAC TATTATTACA TATATCATTA TTATATAAAT    3840

CATGATGCTA GCCAGCAAAG ATGTGAAAAT ATCTGCTCAA AACTTTCAAA GTTTAGTAAG    3900

TTTTTCTTCA TGAGGCCACC AGTAAAAGAC ATTAATGAGA ATTCCTTAGC AAGGATTTTG    3960

TAAGAAGTTT CTTAAACATT GTCAGTTAAC ATCACTCTTG TCTGGCAAAA GAAAAAAAAT    4020

AGACTTTTTC AACTCAGCTT TTTGAGACCT GAAARAATTA TTATGTAAAT TTTGCAATGT    4080

TAAAGATGCA CAGAATATGT ATGTATAGTT TTTACCACAG TGGATGTATA ATACCTTGGC    4140

ATCTTGTGTG ATGTTTAACA CACATGAGGG CTGGTGTTCA TTAATACTGT TTTCTAATTT    4200

TTCCATGGTT AATCTATAAT TAATTACTTC ACTAAACAAA CAAATTAAGA TGTTCAGATA    4260

ATTGAATAAG TACCTTTGTG TCCTTGTTCA TTTATATCGC TGGCCAGCAT TATAAGCAGG    4320

TGTATACTTT TAGCTTGTAG TTCCATGTAC TGTAAATATT TTTCACATAA AGGGAACAAA    4380

TGTCTAGTTT TATTTGTATA GGAAATTTGC CCTGACCCTA ATAATACAT  TTTGAAATGA    4440

AACAAGCTTA AAAAAAAAA  AAAAAAAAAA AAAAAAAAA  AG                       4482

(2) INFORMATION FOR SEQ ID NO:2:

(i) SEQUENCE CHARACTERISTICS:
        (A) LENGTH: 1132 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE:

(xi) SEQUENCE DESCRIPTION: SEQ ID NO:2:

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Gly
    50                  55                  60

Glu Glu Ile Cys Ile Ala Ala Ser Lys Ala Cys Gly Ile Thr Pro Val
65                  70                  75                  80
```

```
Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Thr Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Gln Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
    370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Glu Glu Tyr Asn Leu
    450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495
```

-continued

```
Lys Cys Cys Pro Pro Lys Pro Lys Asp Lys Ser Asn Leu Leu Val Phe
            500             505             510
Arg Thr Asn Gly Val Ser Asp Val Pro Thr Ser Pro Thr Leu Gln Arg
        515             520             525
Pro Thr His Met Asn Gln Met Val Phe His Lys Ile Arg Asn Glu Asp
    530             535             540
Leu Ile Phe Asn Glu Ser Leu Gly Gln Gly Thr Phe Thr Lys Ile Phe
545             550             555             560
Lys Gly Val Arg Arg Glu Val Gly Asp Tyr Gly Gln Leu His Glu Thr
                565             570             575
Glu Val Leu Leu Lys Val Leu Asp Lys Ala His Arg Asn Tyr Ser Glu
            580             585             590
Ser Phe Phe Glu Ala Ala Ser Met Met Ser Lys Leu Ser His Lys His
        595             600             605
Leu Val Leu Asn Tyr Gly Val Cys Val Cys Gly Asp Glu Asn Ile Leu
    610             615             620
Val Gln Glu Phe Val Lys Phe Gly Ser Leu Asp Thr Tyr Leu Lys Lys
625             630             635             640
Asn Lys Asn Cys Ile Asn Ile Leu Trp Lys Leu Glu Val Ala Lys Gln
                645             650             655
Leu Ala Trp Ala Met His Phe Leu Glu Glu Asn Thr Leu Ile His Gly
            660             665             670
Asn Val Cys Ala Lys Asn Ile Leu Leu Ile Arg Glu Glu Asp Arg Lys
        675             680             685
Thr Gly Asn Pro Pro Phe Ile Lys Leu Ser Asp Pro Gly Ile Ser Ile
    690             695             700
Thr Val Leu Pro Lys Asp Ile Leu Gln Glu Arg Ile Pro Trp Val Pro
705             710             715             720
Pro Glu Cys Ile Glu Asn Pro Lys Asn Leu Asn Leu Ala Thr Asp Lys
                725             730             735
Trp Ser Phe Gly Thr Thr Leu Trp Glu Ile Cys Ser Gly Gly Asp Lys
            740             745             750
Pro Leu Ser Ala Leu Asp Ser Gln Arg Lys Leu Gln Phe Tyr Glu Asp
        755             760             765
Arg His Gln Leu Pro Ala Pro Lys Trp Ala Glu Leu Ala Asn Leu Ile
    770             775             780
Asn Asn Cys Met Asp Tyr Glu Pro Asp Phe Arg Pro Ser Phe Arg Ala
785             790             795             800
Ile Ile Arg Asp Leu Asn Ser Leu Phe Thr Pro Asp Tyr Glu Leu Leu
                805             810             815
Thr Glu Asn Asp Met Leu Pro Asn Met Arg Ile Gly Ala Leu Gly Phe
            820             825             830
Ser Gly Ala Phe Glu Asp Arg Asp Pro Thr Gln Phe Glu Glu Arg His
        835             840             845
Leu Lys Phe Leu Gln Gln Leu Gly Lys Gly Asn Phe Gly Ser Val Glu
    850             855             860
Met Cys Arg Tyr Asp Pro Leu Gln Asp Asn Thr Gly Glu Val Val Ala
865             870             875             880
Val Lys Lys Leu Gln His Ser Thr Glu Glu His Leu Arg Asp Phe Glu
                885             890             895
Arg Glu Ile Glu Ile Leu Lys Ser Leu Gln His Asp Asn Ile Val Lys
            900             905             910
Tyr Lys Gly Val Cys Tyr Ser Ala Gly Arg Arg Asn Leu Lys Leu Ile
```

-continued

```
               915                 920                 925
Met Glu Tyr Leu Pro Tyr Gly Ser Leu Arg Asp Tyr Leu Gln Lys His
        930                 935                 940
Lys Glu Arg Ile Asp His Ile Lys Leu Leu Gln Tyr Thr Ser Gln Ile
945                 950                 955                 960
Cys Lys Gly Met Glu Tyr Leu Gly Thr Lys Arg Tyr Ile His Arg Asp
                965                 970                 975
Leu Ala Thr Arg Asn Ile Leu Val Glu Asn Glu Asn Arg Val Lys Ile
                980                 985                 990
Gly Asp Phe Gly Leu Thr Lys Val Leu Pro Gln Asp Lys Glu Tyr Tyr
                995                1000                1005
Lys Val Lys Glu Pro Gly Glu Ser Pro Ile Phe Trp Tyr Ala Pro Glu
       1010                1015                1020
Ser Leu Thr Glu Ser Lys Phe Ser Val Ala Ser Asp Val Trp Ser Phe
 025                1030                1035                1040
Gly Val Val Leu Tyr Glu Leu Phe Thr Tyr Ile Glu Lys Ser Lys Ser
               1045                1050                1055
Pro Pro Ala Glu Phe Met Arg Met Ile Gly Asn Asp Lys Gln Gly Gln
               1060                1065                1070
Met Ile Val Phe His Leu Ile Glu Leu Leu Lys Asn Asn Gly Arg Leu
               1075                1080                1085
Pro Arg Pro Asp Gly Cys Pro Asp Glu Ile Tyr Met Ile Met Thr Glu
      1090                1095                1100
Cys Trp Asn Asn Asn Val Asn Gln Arg Pro Ser Phe Arg Asp Leu Ala
 105                1110                1115                1120
Leu Arg Val Asp Gln Ile Arg Asp Asn Met Ala Gly
               1125                1130

(2) INFORMATION FOR SEQ ID NO:3:

(i) SEQUENCE CHARACTERISTICS:
        (A) LENGTH: 1129 amino acids
        (B) TYPE: amino acid
        (C) STRANDEDNESS: single
        (D) TOPOLOGY: linear (xi) SEQUENCE DESCRIPTION: SEQ ID NO:3:

Met Gly Met Ala Cys Leu Thr Met Thr Glu Met Glu Ala Thr Ser Thr
  1               5                  10                  15
Ser Pro Val His Gln Asn Gly Asp Ile Pro Gly Ser Ala Asn Ser Val
               20                  25                  30
Lys Gln Ile Glu Pro Val Leu Gln Val Tyr Leu Tyr His Ser Leu Gly
           35                  40                  45
Gln Ala Glu Gly Glu Tyr Leu Lys Phe Pro Ser Gly Glu Tyr Val Ala
       50                  55                  60
Glu Glu Ile Cys Val Ala Ala Ser Lys Ala Cys Gly Ile Thr Pro Val
 65                  70                  75                  80
Tyr His Asn Met Phe Ala Leu Met Ser Glu Thr Glu Arg Ile Trp Tyr
                85                  90                  95
Pro Pro Asn His Val Phe His Ile Asp Glu Ser Thr Arg His Asp Ile
               100                 105                 110
Leu Tyr Arg Ile Arg Phe Tyr Phe Pro His Trp Tyr Cys Ser Gly Ser
           115                 120                 125
Ser Arg Thr Tyr Arg Tyr Gly Val Ser Arg Gly Ala Glu Ala Pro Leu
       130                 135                 140
```

```
Leu Asp Asp Phe Val Met Ser Tyr Leu Phe Val Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Lys Asp Gln Thr Pro Leu Ala Val Tyr Asn Ser Val Ser Tyr Lys Thr
        195                 200                 205

Phe Leu Pro Lys Cys Val Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Gln Phe Glu Val
            260                 265                 270

Lys Glu Ser Ala Arg Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Val Gln Leu Tyr Cys Asp Phe
305                 310                 315                 320

Pro Asp Ile Ile Asp Val Ser Ile Lys Gln Ala Asn Gln Glu Cys Ser
                325                 330                 335

Asn Glu Ser Arg Ile Val Thr Val His Lys Gln Asp Gly Lys Val Leu
            340                 345                 350

Glu Ile Glu Leu Ser Ser Leu Lys Glu Ala Leu Ser Phe Val Ser Leu
        355                 360                 365

Ile Asp Gly Tyr Tyr Arg Leu Thr Ala Asp Ala His His Tyr Leu Cys
    370                 375                 380

Lys Glu Val Ala Pro Pro Ala Val Leu Glu Asn Ile His Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Gly Glu Tyr Asn Leu
    450                 455                 460

Ser Gly Thr Asn Arg Asn Phe Ser Asn Leu Lys Asp Leu Leu Asn Cys
465                 470                 475                 480

Tyr Gln Met Glu Thr Val Arg Ser Asp Ser Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Ile Ser Asp Val Gln Ile Ser Pro Thr Leu Gln Arg
        515                 520                 525

His Asn Asn Val Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Lys Thr
```

-continued

```
                565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Gln Leu Ser His Lys His
        595                 600                 605
Leu Val Leu Asn Tyr Gly Val Cys Val Cys Gly Glu Glu Asn Ile Leu
    610                 615                 620
Val Gln Glu Phe Val Lys Phe Gly Ser Leu Asp Thr Tyr Leu Lys Lys
625                 630                 635                 640
Asn Lys Asn Ser Ile Asn Ile Leu Trp Lys Leu Gly Val Ala Lys Gln
                645                 650                 655
Leu Ala Trp Ala Met His Phe Leu Glu Glu Lys Ser Leu Ile His Gly
            660                 665                 670
Asn Val Cys Ala Lys Asn Ile Leu Leu Ile Arg Glu Glu Asp Arg Arg
        675                 680                 685
Thr Gly Asn Pro Pro Phe Ile Lys Leu Ser Asp Pro Gly Ile Ser Ile
    690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
                725                 730                 735
Trp Ser Phe Gly Thr Thr Leu Trp Glu Ile Cys Ser Gly Gly Asp Lys
            740                 745                 750
Pro Leu Ser Ala Leu Asp Ser Gln Arg Lys Leu Gln Phe Tyr Glu Asp
        755                 760                 765
Lys His Gln Leu Pro Ala Pro Lys Trp Thr Glu Leu Ala Asn Leu Ile
    770                 775                 780
Asn Asn Cys Met Asp Tyr Glu Pro Asp Phe Arg Pro Ala Phe Arg Ala
785                 790                 795                 800
Val Ile Arg Asp Leu Asn Ser Leu Phe Thr Pro Asp Tyr Glu Leu Leu
                805                 810                 815
Thr Glu Asn Asp Met Leu Pro Asn Met Arg Ile Gly Ala Leu Gly Phe
            820                 825                 830
Ser Gly Ala Phe Glu Asp Arg Asp Pro Thr Gln Phe Glu Glu Arg His
        835                 840                 845
Leu Lys Phe Leu Gln Gln Leu Gly Lys Gly Asn Phe Gly Ser Val Glu
    850                 855                 860
Met Cys Arg Tyr Asp Pro Leu Gln Asp Asn Thr Gly Glu Val Val Ala
865                 870                 875                 880
Val Lys Lys Leu Gln His Ser Thr Glu Glu His Leu Arg Asp Phe Glu
                885                 890                 895
Arg Glu Ile Glu Ile Leu Lys Ser Leu Gln His Asp Asn Ile Val Lys
            900                 905                 910
Tyr Lys Gly Val Cys Tyr Ser Ala Gly Arg Arg Asn Leu Arg Leu Ile
        915                 920                 925
Met Glu Tyr Leu Pro Tyr Gly Ser Leu Arg Asp Tyr Leu Gln Lys His
    930                 935                 940
Lys Glu Arg Ile Asp His Lys Lys Leu Leu Gln Tyr Thr Ser Gln Ile
945                 950                 955                 960
Cys Lys Gly Met Glu Tyr Leu Gly Thr Lys Arg Tyr Ile His Arg Asp
                965                 970                 975
Leu Ala Thr Arg Asn Ile Leu Val Glu Asn Glu Asn Arg Val Lys Ile
            980                 985                 990
```

```
-continued

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro Gln
    1010                1015                1020

Ser Leu Thr Glu Ser Lys Phe Ser Val Ala Ser Asp Val Trp Ser Phe
025                 1030                1035                1040

Gly Val Val Leu Tyr Glu Leu Phe Thr Tyr Ile Glu Lys Ser Lys Ser
                1045                1050                1055

Pro Pro Val Glu Phe Met Arg Met Ile Gly Asn Asp Lys Gln Gly Gln
            1060                1065                1070

Met Ile Val Phe His Leu Ile Glu Leu Leu Lys Ser Asn Gly Arg Leu
        1075                1080                1085

Pro Arg Pro Glu Gly Cys Pro Asp Glu Ile Tyr Val Ile Met Thr Glu
    1090                1095                1100

Cys Trp Asn Asn Asn Val Ser Gln Arg Pro Ser Phe Arg Asp Leu Ser
105                 1110                1115                1120

Phe Gly Trp Ile Lys Cys Gly Thr Val
            1125

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

GGGCGGAAGT GCTCTCGGCG GAAG                                      24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

AGTGTGCTAC AGTGCTGGTC GTCG                                      24
```